United States Patent
Hickman et al.

(10) Patent No.: US 11,697,795 B2
(45) Date of Patent: Jul. 11, 2023

(54) METHOD AND SYSTEM FOR PRINTING CELLS TO A SUBSTRATE COMPRISING CELL ADHESIVE REGIONS

(71) Applicants: University of Central Florida Research Foundation, Inc., Orlando, FL (US); Hesperos, Inc., Orlando, FL (US)

(72) Inventors: James J. Hickman, Orlando, FL (US); Sandra Rothemund, Orlando, FL (US); Megan Aubin, Orlando, FL (US); Frank Alexander, Orlando, FL (US)

(73) Assignees: University of Central Florida Research Foundation, Inc., Orlando, FL (US); Hesperos, Inc., Orlando, FL (US)

( * ) Notice: Subject to any disclaimer, the term of this patent is extended or adjusted under 35 U.S.C. 154(b) by 525 days.

(21) Appl. No.: 16/534,624

(22) Filed: Aug. 7, 2019

(65) Prior Publication Data
US 2020/0048602 A1 Feb. 13, 2020

Related U.S. Application Data

(60) Provisional application No. 62/715,413, filed on Aug. 7, 2018.

(51) Int. Cl.
*C12N 5/00* (2006.01)
*B29C 64/106* (2017.01)

(52) U.S. Cl.
CPC .......... *C12N 5/0068* (2013.01); *B29C 64/106* (2017.08); *C12N 2535/00* (2013.01); *C12N 2537/00* (2013.01); *C12N 2539/00* (2013.01)

(58) Field of Classification Search
None
See application file for complete search history.

(56) References Cited

U.S. PATENT DOCUMENTS

| 7,051,654 B2 | 5/2006 | Boland et al. |
| 2004/0237822 A1* | 12/2004 | Boland ................. B01L 3/0268 101/483 |
| 2015/0219622 A1 | 8/2015 | Hickman |

OTHER PUBLICATIONS

Allig, Sebastian. "Controlled Cell Formation Using Bioprinting." Poster presentation in Prague (May 2018) (Year: 2018).*
Kang et al. "Bioprinted scaffolds for cartilage tissue engineering." Cartilage Tissue Engineering. Humana Press, New York, NY, 2015. 161-169. (Year: 2015).*
Marconi et al. "Emergent functional properties of neuronal networks with controlled topology." PloS One 7.4 (2012): e34648. (Year: 2012).*
Xu et al. "Microengineering methods for cell-based microarrays and high-throughput drug-screening applications." Biofabrication 3.3 (2011): 034101. (Year: 2011).*
Martinez et al. "Controlled single-cell deposition and patterning by highly flexible hollow cantilevers." Lab on a Chip 16.9 (2016): 1663-1674. (Year: 2016).*
Laschke et al. "Life is 3D: boosting spheroid function for tissue engineering." Trends in Biotechnology 35.2 (2017): 133-144. (Year: 2017).*
Davidoff, Sherry N., et al. "The submerged printing of cells onto a modified surface using a continuous flow microspotter." JoVE (Journal of Visualized Experiments) 86 (2014): e51273.

* cited by examiner

*Primary Examiner* — Emily A Cordas
(74) *Attorney, Agent, or Firm* — Meunier Carlin & Curfman LLC

(57) ABSTRACT

The method of culturing cells disclosed herein includes printing cells onto a substrate that includes cell adhesive regions and cell repulsive regions. The cells are suspended in a printing medium to create a cell suspension, and a volume of the cell suspension is loaded into a printer. A cell adhesive region of the substrate is aligned beneath the printing channel of the printer, and droplets of the cell suspension are dispensed from the printing channel directly onto the cell adhesive region. Contact of the dispensed droplets with cell repulsive regions of the substrate is limited, either by targeting of the droplets to the cell adhesive regions, by repulsions generated by the cell repulsive areas, or both. The cells adhere to the cell adhesive regions to create a cell pattern, and are maintained thereafter in a physiologically suitable environment.

23 Claims, 20 Drawing Sheets

METHOD AND SYSTEM FOR PRINTING CELLS TO A SUBSTRATE COMPRISING CELL ADHESIVE REGIONS

STATEMENT REGARDING FEDERALLY SPONSORED RESEARCH OR DEVELOPMENT

This application claims the benefit of U.S. Provisional Application No. 62/715,413, filed on Aug. 7, 2018, which is incorporated herein by reference in its entirety.

This invention was made with Government Support under Contract No. 1R44TR001326-01A1 and Grant No. R01NS050452, both awarded by the National Institutes of Health. The Government has certain rights in the invention.

BACKGROUND

The current fabrication of biological microelectromechanical systems (bioMEMs) often includes a process of plating cells onto substrates that include sensors. The sensors provide information to the researcher regarding the function of the cells. Sensors can include, for example, microelectrode arrays for measuring cell electrical activity and cantilevers for measuring cell forces. The plating of cells onto bioMEM sensors typically results in the loss of the cells that do not adhere to the plate. Furthermore, cells that adhere to the plate in locations not measured by the sensors are not used in the experiments. Given the high cost and extensive time associated with certain types of cell culture, the loss of these cells presents a problem.

DETAILED DESCRIPTION

Figure 1:
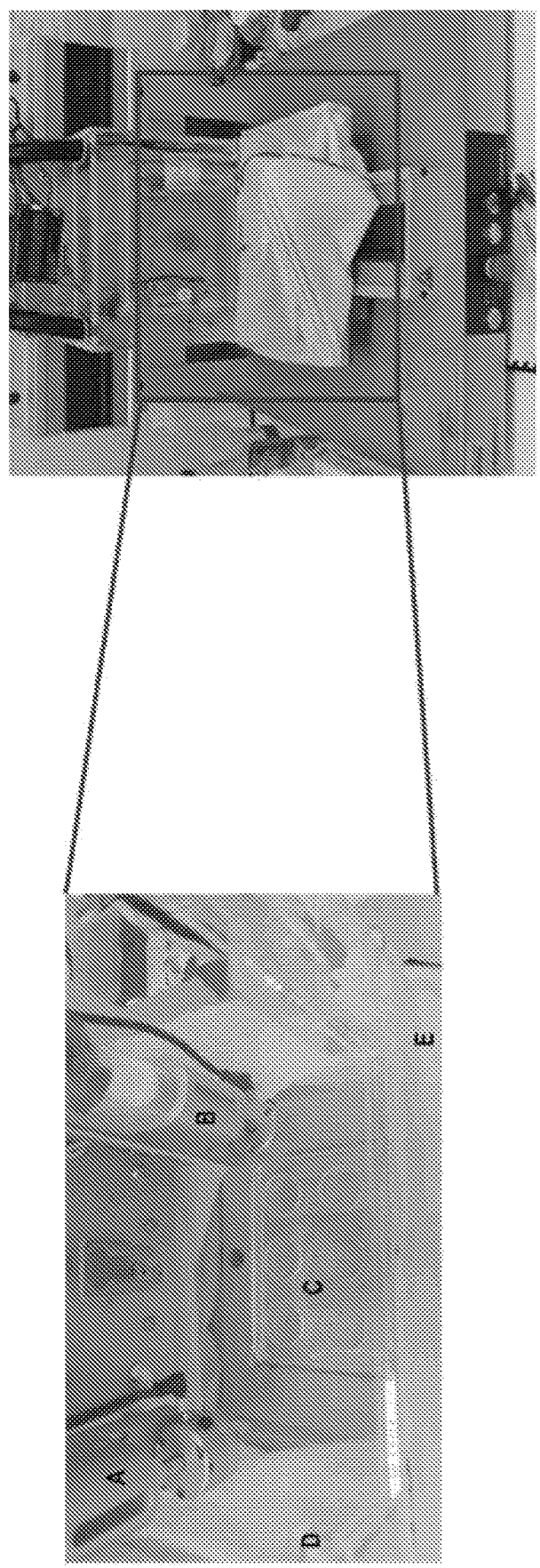
FIG. 1 shows a bioprinter and its modifications for printing cells on surfaces. A. Print cartridge holding first cell suspension. B. Print cartridge holding media or second cell suspension. C. Plate holding surfaces. D. Plastic encasement surrounding the print area to keep the environment sterile and humid. E. Latex material to complete the print area enclosure while allowing for movement of the stage and frame during printing.

Terms used throughout this application are to be construed with ordinary and typical meaning to those of ordinary skill in the art. However, Applicant desires that the following terms be given the particular definition as defined below.

As used in the specification and claims, the singular form "a," "an," and "the" include plural references unless the context clearly dictates otherwise. For example, the term "a cell" includes a plurality of cells, including mixtures thereof. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

"Exemplary" means "an example of" and is not intended to convey an indication of a preferred or ideal embodiment. "Such as" is not used in a restrictive sense, but for explanatory purposes.

The unique method disclosed herein creates precisely positioned cell patterns (micrometer range) in a 2D or 3D environment. In this regard, the combination of advanced surface chemistry procedures and an efficient bioprinting technique suitable for various cell types is used to produce specific cell patterns on functional surfaces that can be integrated onto microfluidic devices such as biological microelectromechanical systems (BioMEMS).

The emerging field of bioprinting shows great potential to design complex structures mimicking the physiological environment of tissues and organs that can be used for 3D cell culture, in vitro disease models or tissue engineering. Usually cells are either encapsulated in a biological or chemical hydrogel or printed layer-by-layer to obtain a construct with mechanical stability and a biochemical microenvironment allowing stimulation of specific cell functions. The bioprinting method described herein allows printing of cells from a cell suspension in cell culture media (containing serum or under serum free conditions) without the need of a hydrogel or bioink that would be required for scaffold support. The print parameters and conditions can be adjusted leading to a robust and flexible method applicable for both animal and human cell types including but not limited to neurons, muscle cells, cardiomyocytes, hepatocytes, kidney cells, epithelial and endothelial cells (specifically NG108, C2C12, iPSC and spinal cord derived human motoneurons, rat and human cardiac cells, human primary muscle cells). The printing procedure can be conducted with cells obtained from cell lines, primary cells, as well as induced pluripotent stem cell (iPSC) derived and spinal cord derived cells. It enables printing of a cell suspension with volumes down to the nanoliter range whereas the positioning of the dispensed cells can be precisely controlled in the micrometer range on the respective functional substrate.

The functional substrates include but are not limited to coverslips, multielectrode arrays or cantilevers and can be biologically modified (for example by coating with ECM proteins), chemically modified (including but not limited to various surface chemistry procedures such as silanization, click chemistry, photolithography) or a combination thereof, depending on the cell types and the desired application. Thus, non-patterned and patterned surfaces can be generated improving the adherence, growth and localization of the printed cells. Exemplary substrates that could be printed with cells using the methods disclosed herein are described in U.S. Patent Application Publication No. 2015/0219622, the disclosure of which is incorporated by reference in its entirety.

The method of culturing cells disclosed herein includes printing cells onto a substrate that includes cell adhesive regions and cell repulsive regions. The cells are suspended in a printing medium to create a cell suspension, and a volume of the cell suspension is loaded into a cell printer. A cell adhesive region of the substrate is aligned beneath the printing channel of the printer, and droplets of the cell suspension are dispensed from the printing channel directly onto the cell adhesive region. Contact of the dispensed droplets with cell repulsive regions of the substrate is limited, either by targeting of the droplets to the cell adhesive regions, by repulsions generated by the cell repulsive areas, or both. The cells adhere to the cell adhesive regions to create a cell pattern, and are maintained thereafter in a physiologically suitable environment.

The substrate is patterned with one or more chemical layers to form cell adhesive regions and cell repulsive regions prior to initiating cell printing. The cell adhesive regions can include, for example, any factor that promotes cell adhesion. For example, the cell adhesive regions can include, but are not limited to including, natural or naturally derived proteins (such as those found in the extracellular matrix), peptides derived from natural or naturally proteins, integrin binding molecules, cell adhesion molecules (including cadherins (e.g., E-cadherin, N-cadherin, P-cadherin, K-cadherin, R-cadherin, VE-cadherin, LI cadherindesmoglein (DSG)1, DSG2, DSG3, DSG4, desmocolin (DSC)1, DSC2, and DSC3), selectins (e.g., E-selectin, P-selectin, L-selectin), integrins (e.g., $\alpha_1\beta_1$ integrins, LFA1, and MAC-1)), synthetic materials (such as, but not limited to, polymers or hydrogels) that are modified to or naturally promote cell adhesion, synthetic materials that are modified with naturally derived proteins, peptides, or molecules, or any combination thereof. In some embodiments, the surface itself may be cell adhesive without modification. In one aspect, the cell adhesive region can comprise DETA.

A cell repulsive layer may also be patterned onto the substrate. The cell repulsive layer can include any modification that prevents cells from adhering to the surface. In some embodiments, for example, the surface can be coated with polyethylene glycol (PEG), or a material that includes polyethylene glycol, to prevent cell adhesion. In addition to PEG, examples of materials that can be used to create repulsive layer include, but are not limited to J1/Tenascin, EphrinB2, chondroitin sulfate proteoglycan (CSPG), fibronectin and leucine-rich transmembrane protein-2 (FLRT2), and/or albumin. In some embodiments, no chemical modification is necessary because the surface itself is cell repulsive.

The patterned substrate may be fabricated on the same day as the cells are printed, or it may be fabricated days to years prior to cell printing, so long as it is stored in a manner that preserves the cell adhesive and cell repulsive properties of those respective regions. In some embodiments, the cell adhesive regions can be positioned over sensors (such as, for example, microelectrode arrays or cantilevers). The sensors provide feedback on the cell properties during culture.

A benefit of the disclosed method is that high resolutions of cell patterning can be obtained. For example, in some embodiments, the cell pattern can have length or width dimensions that are less than 1 millimeter, including less than 0.9 millimeters, less than 0.8 millimeters, less than 0.7 millimeters, less than 0.6 millimeters, less than 0.5 millimeters, less than 0.4 millimeters, less than 0.3 millimeters, less than 0.2 millimeters, and less than 0.1 millimeters.

Cells to be patterned are loaded into a printing medium to create a cell suspension. The printing medium can be any cell culture medium suitable for the survival of the cells suspended therein. In some embodiments, the printing medium is selected to suit the particular type of cell. The cell suspension is highly concentrated with cells to promote efficient patterning. In some embodiments, the concentration of the cell suspension is from 0.5 million to about 30 million cells per milliliter, including 0.5 million/mL, about 1 million/mL, about 5 million/mL, about 10 million/mL, about 15 million/mL, about 20 million/mL, about 25 million/mL, and about 30 million cells/mL.

One or more cell types may be loaded into the printing medium to create the cell suspension. In some embodiments, multiple cell types can be printed onto a single surface with high resolution, thereby creating a cell pattern with multiple cell types.

In some embodiments, the print medium comprises an agent to prevent cell settling when the cell suspension is in the printing cartridge, prior to printing. Prevention of cell settling helps to ensure that the consistency of the spacing of the cells once they are printed onto the substrate. In some embodiments, the agent that prevents cell settling can be is a density gradient medium. An example density gradient medium is OptiPrep™ (Sigma, St. Louis, Mo.), which is manufactured as a 60% (w/v) solution of iodixanol in water, but other density gradient mediums can also be used as the agent to prevent cell settling. The methods can include, for example, diluting OptiPrep™ to about 5% (v/v) in the printing medium to prevent cell settling, including diluting OptiPrep™ to about 1% (v/v), about 2% (v/v), about 3% (v/v), about 4% (v/v), about 5% (v/v), about 6% (v/v), about 7% (v/v), about 8% (v/v), about 9% (v/v), or about 10% (v/v) in the printing medium.

The method advantageously does not require that a bioink, or hydrogel, be incorporated into the printing medium. As such, the print medium has a viscosity of less than about 5 centipoise at 37 degrees Celsius, including less than about 4 centipoise, less than about 3 centipoise, less than about 2 centipoise, and less than about 1 centipoise at 37 degrees Celsius. By contrast, a typical 1% collagen solution (prior to gelling) is about 96 centipoise at 37 degrees Celsius. The exclusion of the bioink saves materials and expense.

The dispensed droplets of cells can have very small volumes, contributing to the high resolution of the method. For example, in some embodiments, the printed volume of a single printed droplet is less than about 2 microliters, including less than about 1.5 microliters, less than about 0.5 microliters, less than about 0.1 microliters, less than about 0.09 microliters, less than about 0.08 microliters, less than about 0.07 microliters, less than about 0.06 microliters, less than about 0.05 microliters, less than about 0.04 microliters, and less than about 0.03 microliters. In some embodiments, the volume of a single printed droplet is about 0.02 microliters. These small volumes help to confine the deposition of the droplets to the cell adhesive surfaces.

The combination of all of the cell adhesive regions make up a region that has a total cell adhesive surface area. The method includes dispensing a volume of about 0.05 microliters to about 2 microliters of cell suspension per square millimeter of the total cell adhesive surface area, including about 0.05 microliters, about 0.2 microliters, about 0.4 microliters, about 0.6 microliters, about 0.8 microliters, about 1 microliters, about 1.2 microliters, about 1.4 microliters, about 1.6 microliters, about 1.8 microliters, and about 2 microliters per square millimeter of the total cell adhesive surface area. The total number of dispensed cells is from about 500 cells per square millimeter of the total cell adhesive surface area to about 2,000 cells per square millimeter of the total cell adhesive surface area, including about 500 cells, about 750 cells, about 1,000 cells, about 1,250 cells, about 1,500 cells, about 1,750 cells and about 2,000 cells per square millimeter of the total cell adhesive surface area. The total number of cells required is relatively small compared to conventional hand plating methods that do not permit the delivery of such small droplet volumes. Because the droplets of cell suspension are applied only to the small cell adhesive areas, the total number of cells needed is relatively low.

The printer is able to target the cell adhesive areas with high precision. In a preferred embodiment, the contact region between a droplet dispensed from the printing channel and the underlying substrate is 100% positioned on a cell adhesive surface. Should the contact region between the droplet and the substrate be at all removed from the cell adhesive region, in preferred embodiments greater than 80% of the area of the contacted surface would still be part of a cell adhesive region (including greater than 85%, greater than 90%, and greater than 95% of the area of the contacted surface). Measures can be undertaken to continuously validate the position of the dispensed droplets as they are being dispensed, to limit their contact with the cell repulsive regions. In some embodiments, these measures can include using a camera to view the positioning of the droplets as they are being dispensed or taking measurements from sensors on the substrates to verify that cells are positioned on the sensors.

The methods can include measures to prevent evaporation of the printed droplets. For example, in some embodiments, the environment around the printed droplets can be a humidified environment. For example, the substrate can be positioned on a customized printer plate that includes a water reservoir. The area including the printing channel, the printer plates, and the substrate can be sealed from the outside environment as the cell suspension is dispensed to prevent evaporation.

The method disclosed herein facilitates long term experiments because cells are confined to the regions on or immediately around the sensors and do not migrate or proliferate far from their dispensed positions. This prevents the background noise that can occur when electrically active cell cultures create undefined patterns. For example, a cardiomyoycte culture patterned in a line will send an electrical signal along that line at a predictable conduction velocity, yet a cardiomyocyte culture with no defined pattern sends an electrical signal in all directions at undefined velocities. When the cell adhesive regions are positioned over sensors, the majority of the cells on the substrate remain confined to those positions over the sensors for long periods of time, including greater than 5 days, greater than 10 days, greater than 15 days, greater than 20 days, greater than 25 days, greater than 30 days, greater than 35 days, greater than 40 days, greater than 45 days, and greater than 50 days. As used herein, a "majority" means greater than 50% of the cells of the total cell culture, including greater than 60% of the cells, greater than 70% of the cells, greater than 80% of the cells, greater than 90% of the cells, and greater than 95% of the cells of the total cell culture.

Figure 18:
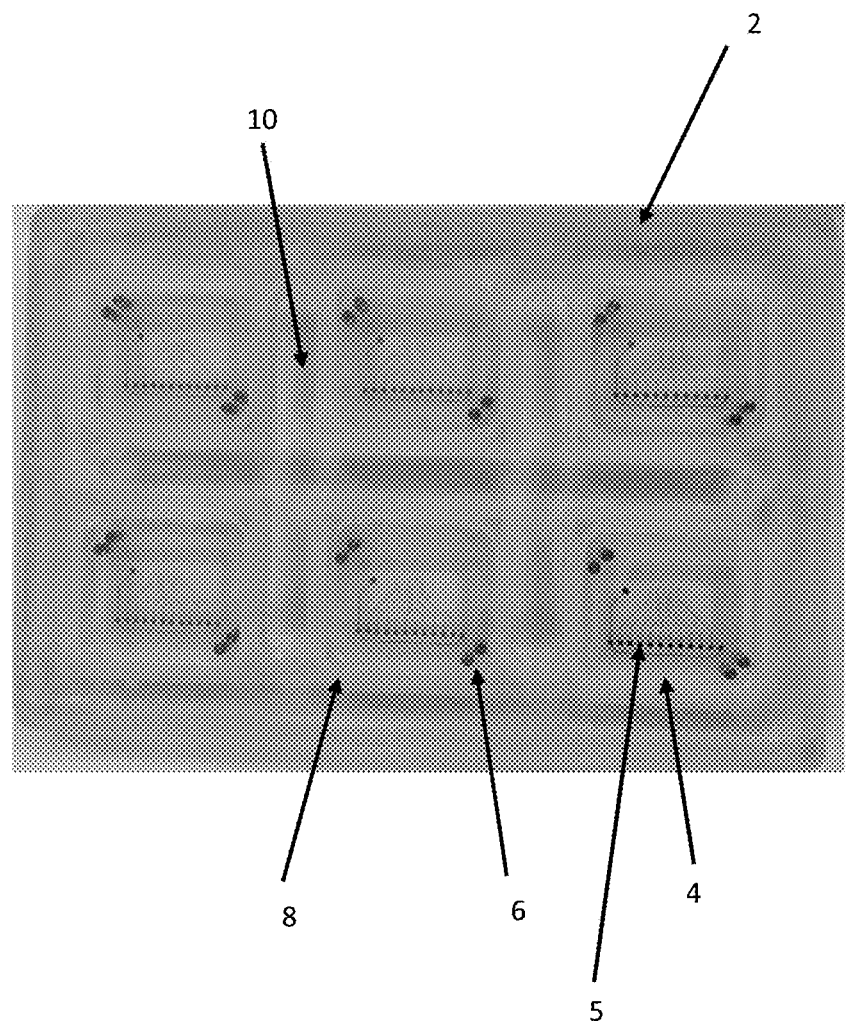
FIG. 18 shows a custom fabricated printer plate including cMEAs and a water reservoir for humidification of the printer chamber.

Systems for supporting cell printing are also disclosed herein. An embodiment of such a system is shown in FIG. 18. The system includes a substrate 4 comprising cell repulsive regions, cell adhesive regions, and at least one sensor 5 positioned beneath a cell adhesive region. The system further includes a plate 2 including a holding region 8. The holding region 8 holds or supports the substrate 4 and a reservoir 10 at least partially surrounding the holding region 8. The top surface area of the substrate 4 is smaller than the top surface area of the holding region 8, so that the substrate 4 fits entirely on the surface of the holding region 8. In the embodiment shown, the holding region 8 is a raised platform, having an upper surface that is higher than the lowest surface of the reservoir 10. One or more securing devices 6 can be included to secure the substrate 4 to the holding region 8. The holding region 8 can, in some embodiments, include walls that define a holding chamber for the substrate. The width of the substrate 4 is smaller than a corresponding inner width of the holding chamber, such that the substrate can be placed and retained within the holding chamber. Some embodiments of the system can also include a bioprinter. The plate 2 is configured to align a cell adhesive region of the substrate 4 with a printing channel of the bioprinter.

In some embodiments, three dimensional cell cultures can be formed. For example, the step of dispensing a plurality of droplets of cell suspension creates a first layer of cells, and additional layers of cells can be patterned on top of the first layer of cells to create a three dimensional cell structure. In some embodiments, proliferation of the first layer of cells is confined to the cell adhesive region, and that proliferation creates a three dimensional cell culture. In some embodiments, a first scaffolding layer (a hydrogel, for example), can be printed on top of the first layer of cells, and then a second layer of cells can be printed on top of the first scaffolding layer, and then a second scaffolding layer can be printed on top of the second layer of cells, and so on. In some embodiments, different materials can be utilized to form different scaffolding layers, and different cells types can be utilized to form different cell layers.

EXAMPLES

Example 1—Bioprinting Experiments

Figure 2:
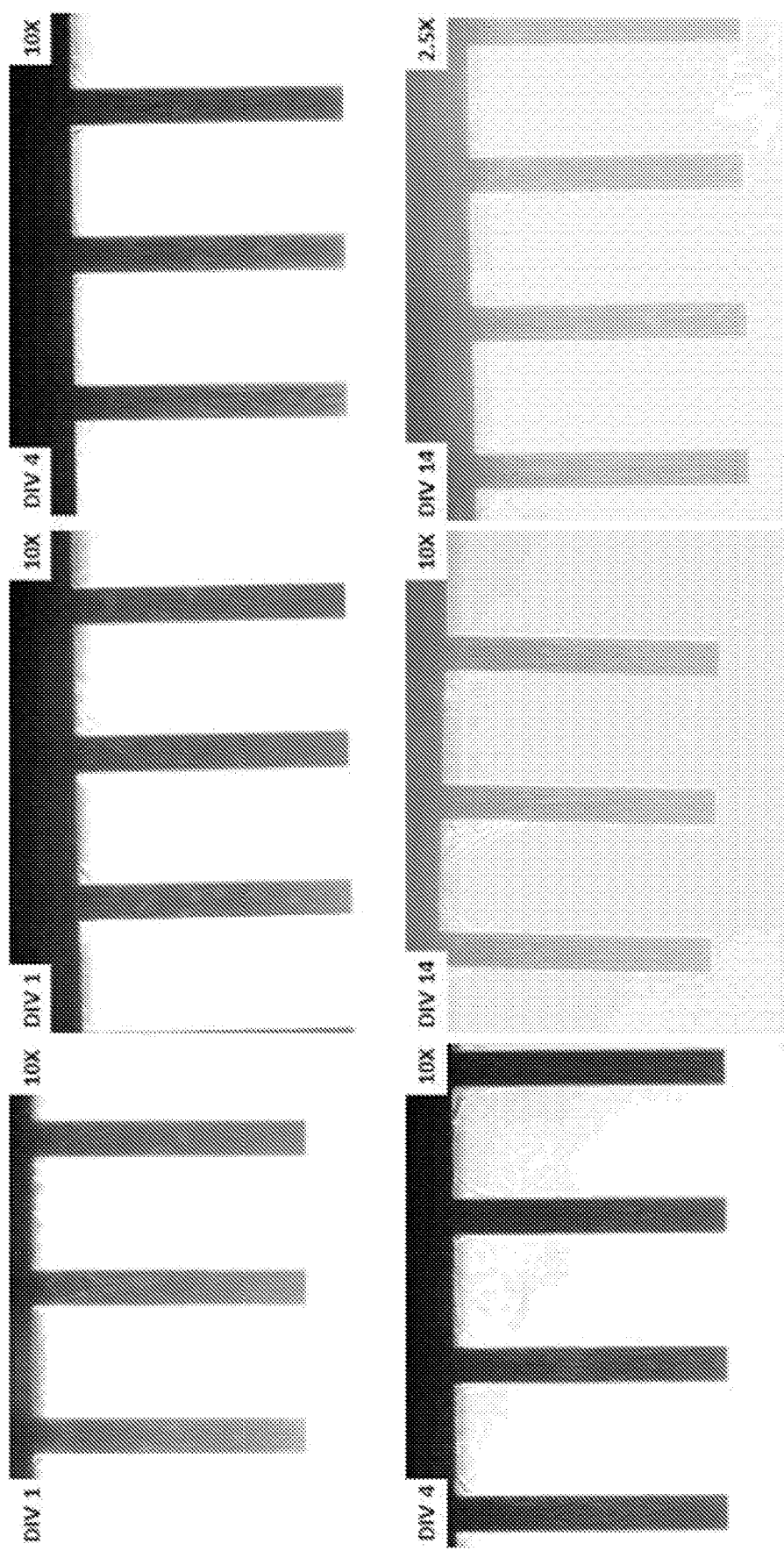
FIG. 2 shows the printing and characterization of human skeletal muscle. The cells were printed from a cell suspension onto silicone cantilevers modified with DETA and cell morphology was studied over a culture period of 14 days after the printing process (days in vitro, DIV) in serum free media.

FIG. 1 shows the 3D bioprinter along with its modifications. FIG. 2 shows the results of printing human skeletal muscle myocytes onto silicon cantilevers followed by differentiation into myotubes over a culture period of 14 days.

Figure 3:
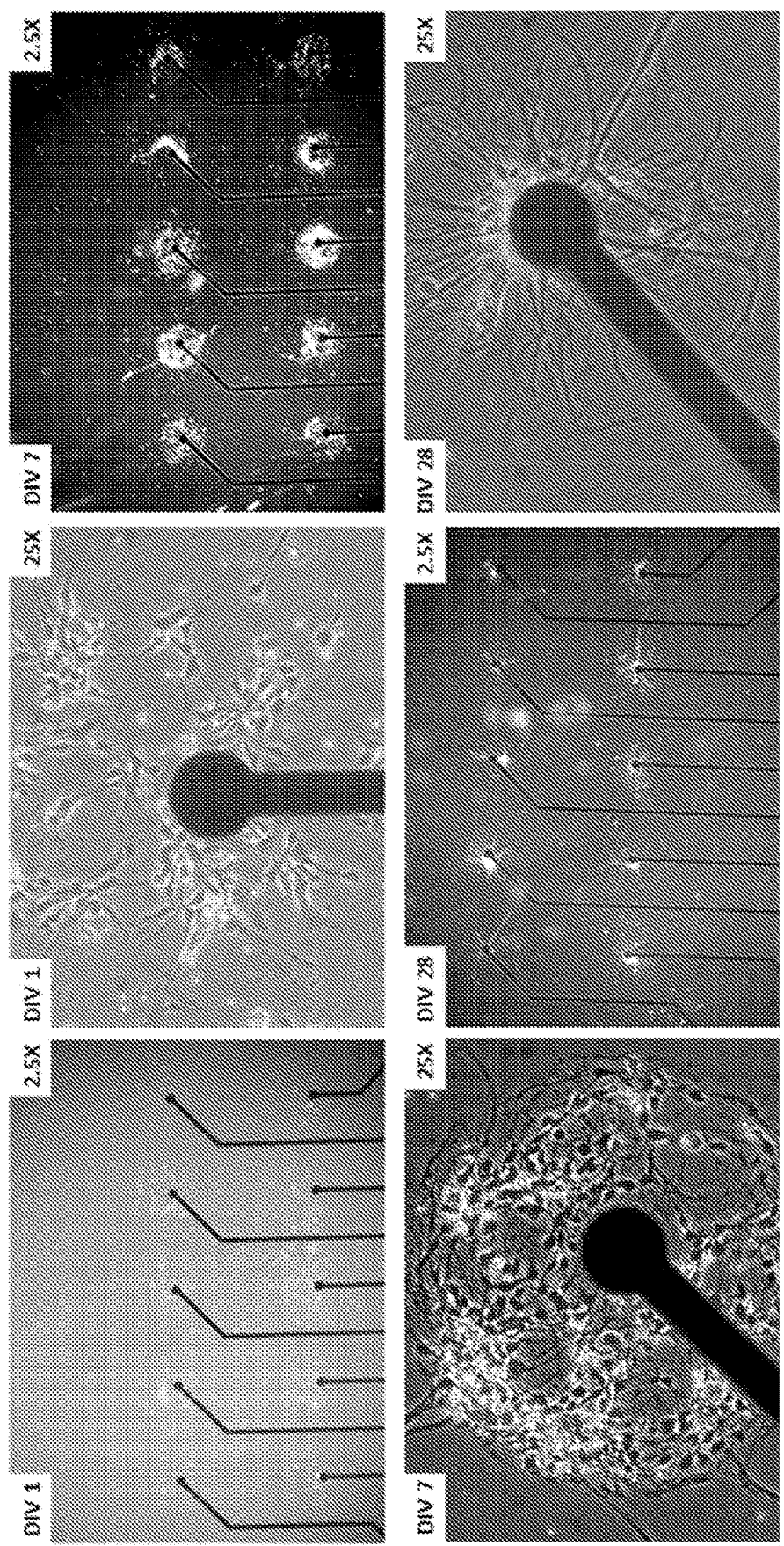
FIG. 3 shows the printing and characterization of spinal cord derived human motoneurons. The cells were printed on custom-fabricated multielectrode arrays with a cell adhesive area (DETA) around the electrodes (500 um diameter) and a cell repulsive area (PEG) covering the remaining surface. Cell morphology was studied over an extended culture period of 28 days after the printing process (DIV) in serum free media.

The effectiveness of the printing method is demonstrated by a considerable decrease of cells required per individual surface to successfully generate the desired cell pattern in comparison to regular hand plating techniques. The printing method enables one to precisely dispense a minimal volume containing a certain amount of cells onto a specific location, for example the cytophilic area around the electrodes of custom-fabricated multielectrode arrays as depicted in FIG. 3. The current hand plating method involves covering the entire surface with a cell suspension, followed by washing off and discarding a huge excess of cells that did not adhere on the cytophobic area of the substrate surface. Since the cell printer deposits cells exactly (and only) on the desired areas, the wasteful "washing off" step is eliminated. The precision that can be achieved with the bioprinter decreases the amount of cells required per surface (up to 80-90% fewer cells per surface) and is therefore expected to reduce the required resources and costs of the experiment. This is especially intriguing when printing cell types where resources are limited and cost effective alternatives are of key importance (for example human iPSC derived cardiomyocytes). Other benefits of cell printing include automated cell deposition thus making scale-up and large thru-put cell plating possible.

Figure 4:
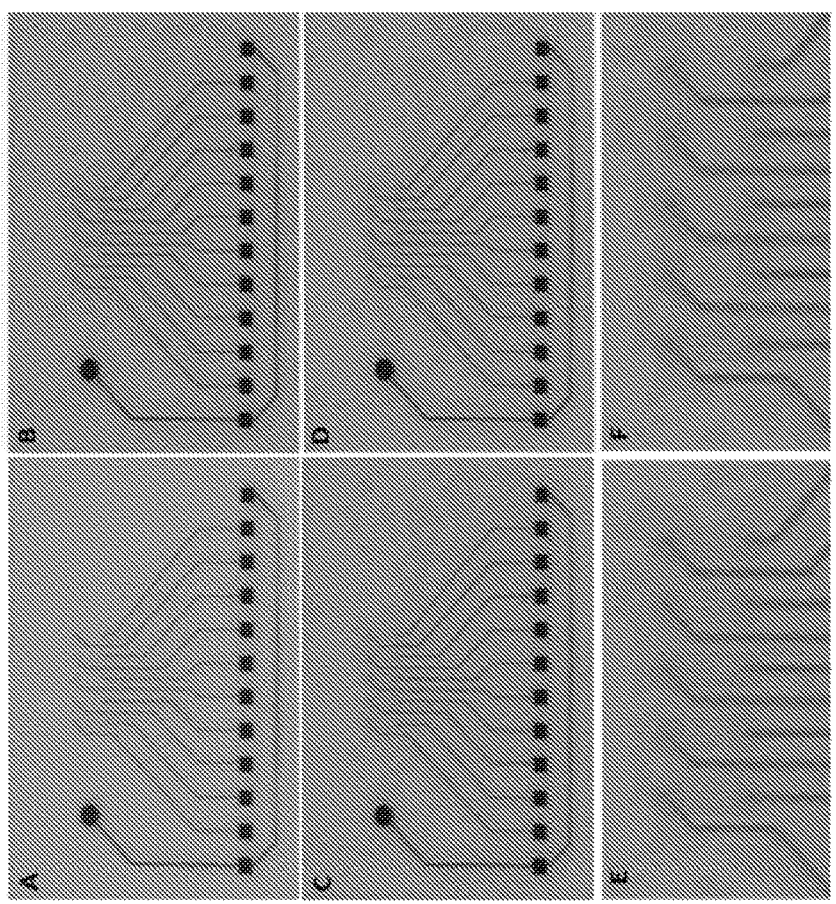
FIG. 4 shows the molecular structure of silanes used for surface modification, DETA and PEG (left) and surface patterning designs for microelectrode arrays (cMEAs, right). A. Blanket DETA coated. B. 500 µm diameter DETA circles over electrodes. C and D. Feed forward pattern with 500 µm diameter DETA circles over electrodes. C. All top to bottom pattern. D. Side to side pattern with one top to bottom pattern. E. Zoomed in view of image C electrodes. F. zoomed in view of image D electrodes.
Figure 4:
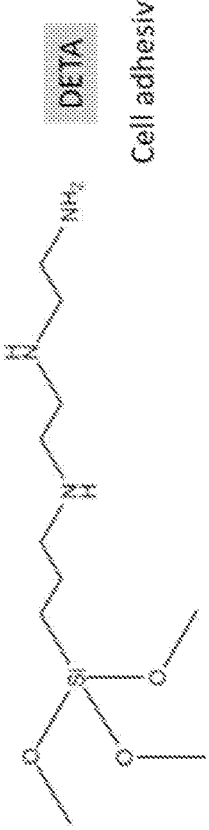
Figure 4:
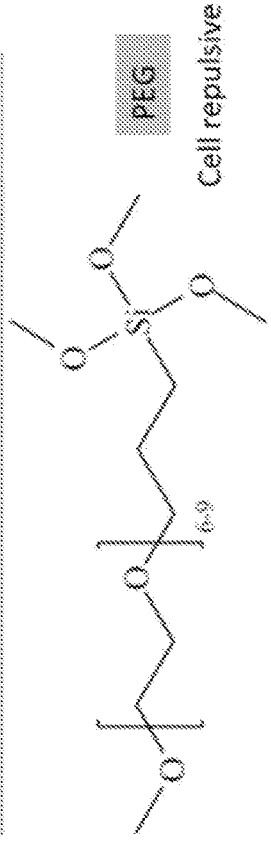

To encourage the cells to grow in a desired location, different patterns were created on the surface of the substrate. FIG. 3 depicts several examples of patterned microelectrode arrays (cMEAs) that were created using the organosilanes N1-(3-rimethoxysilylpropyl)diethylenetriamine (DETA) and 2-[Methoxy(Polyethyleneoxy)6-9Propyl]trimethoxysilane (PEG) thus leading to specific cytophilic areas after treatment with DETA and cytophobic areas after treatment with PEG. The chemical structures and examples of patterns that might be formed with DETA and PEG are shown in FIG. 4. The patterns can be designed for the desired application and cell types. To increase uniformity and reproducibility of the print pattern, the cell suspension loaded into the bioprinter can include an agent that prevents cell settling. Density gradient media, such as OptiPrep™, is conventionally used for cell isolation protocols. By the methods disclosed herein, it can be included in the cell suspension to help to prevent cell settling within the print cartridge, leading to more reproducible and uniform cell patterns.

Figure 5:
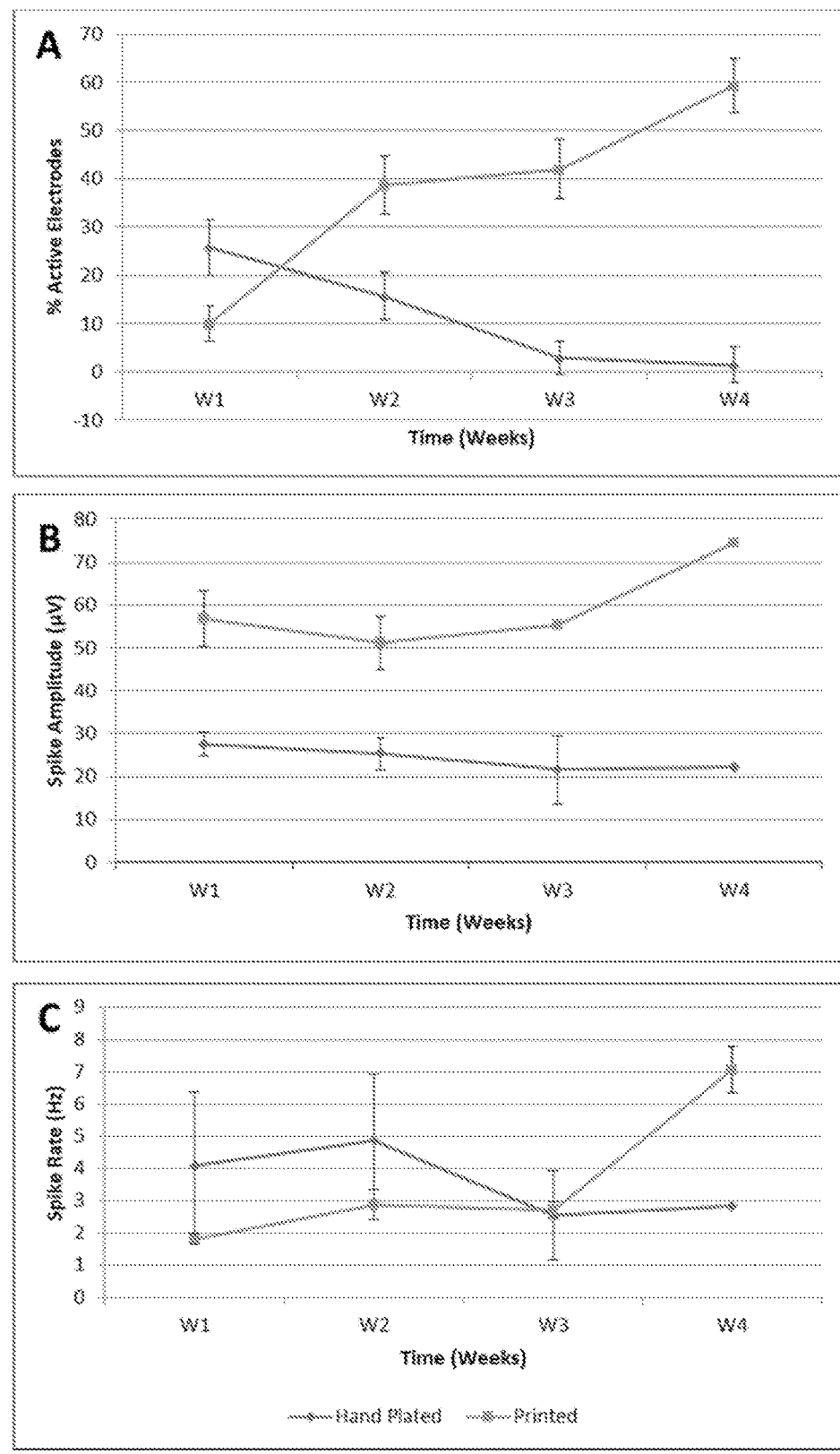
FIG. 5 shows graphs of spontaneous electrical activity of printed and hand plated human motoneurons on patterned cMEAs in systems, blue diamonds represent hand plated system data while orange squares represent printed data. A. Percent of active electrodes. B. Spike amplitude C. Spike rate.
Figure 6:
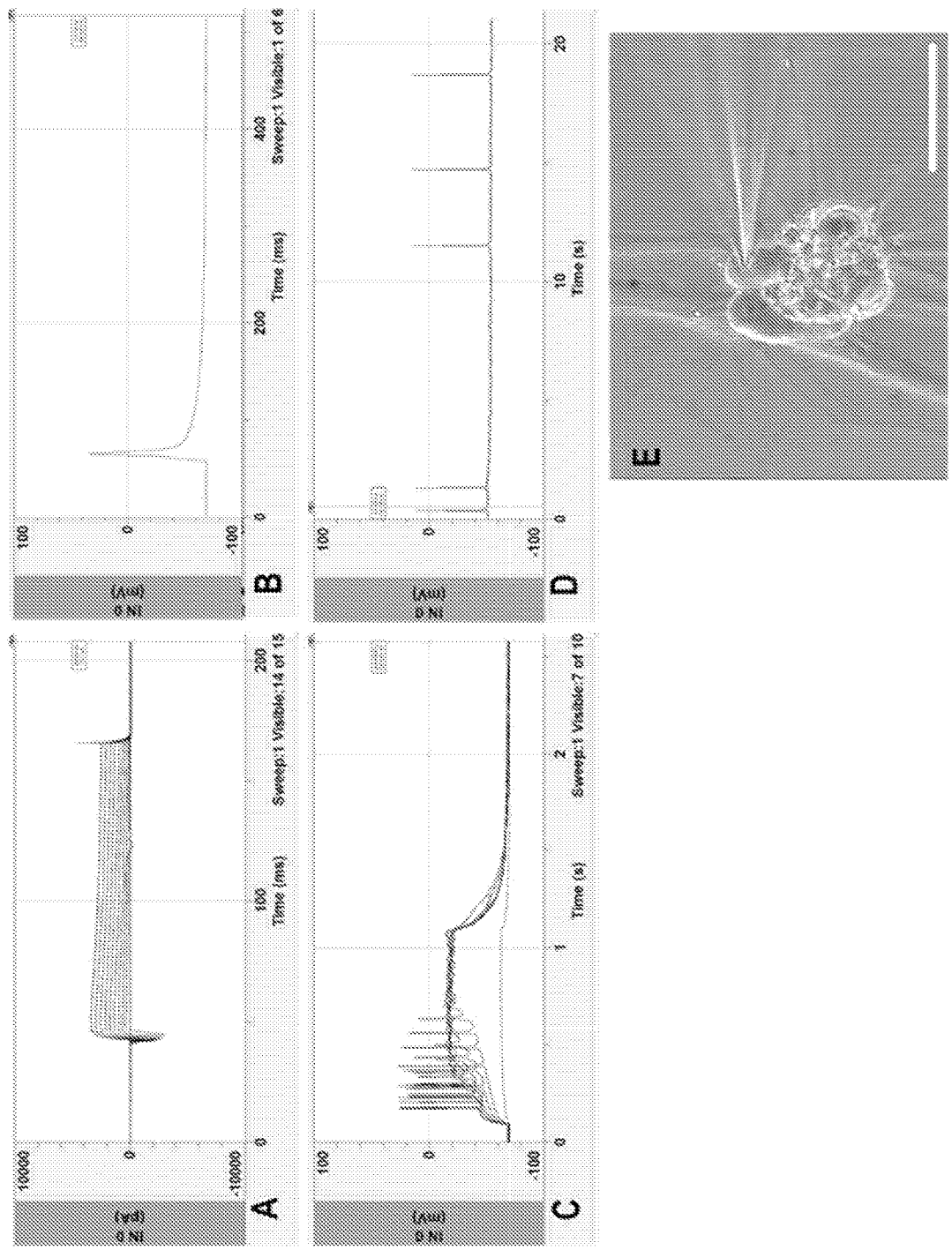
FIG. 6 shows patch clamp data and images for printed human motoneurons on DETA coated glass coverslip twenty-eight days after print. A. Voltage clamp showing inward and outward current through cells. B. Single action potential from cell. C. Current clamp showing repetitive firing. D. Spontaneous activity of cell. E. Image of patching single hMN cell, scale bar 25 µm.

The patterns shown in FIG. 4 were used to print human motoneurons on cMEAs and were cultured for several weeks. The surfaces were assembled into body-on-a-chip systems and spontaneous electrical cellular activity was recorded over a period of twenty-eight days after system assembly of printed cells on patterns, indicating functional neuronal maturation (FIG. 5). The printed cMEAs showed a greater percentage of active electrodes towards the end of the four week period and a greater spike amplitude compared to the hand plated cMEAs. The results of the non-invasive recordings over twenty-eight days were supported by data from patch clamp of printed cells, confirming good cell viability and functionality (FIG. 6).

Figure 7:
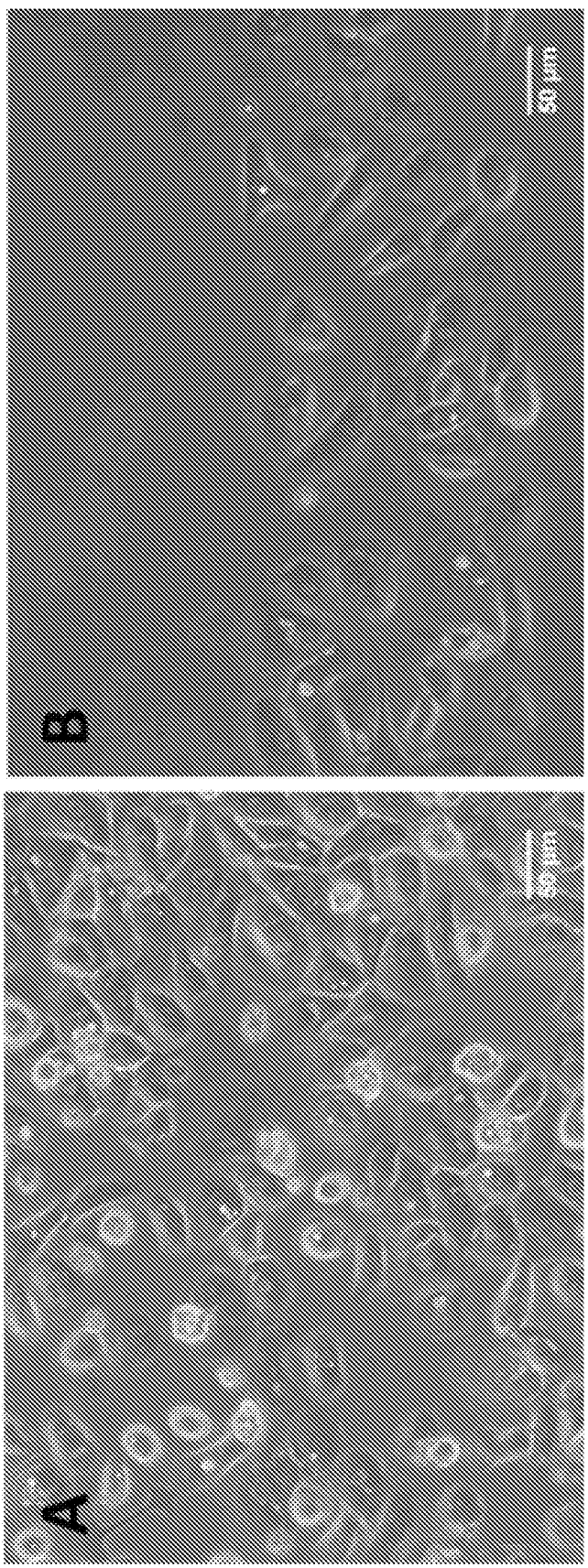
FIG. 7 shows the characterization of cardiac cells one day after plating at 2,500×. A. Hand plate. B. Printed line.
Figure 8:
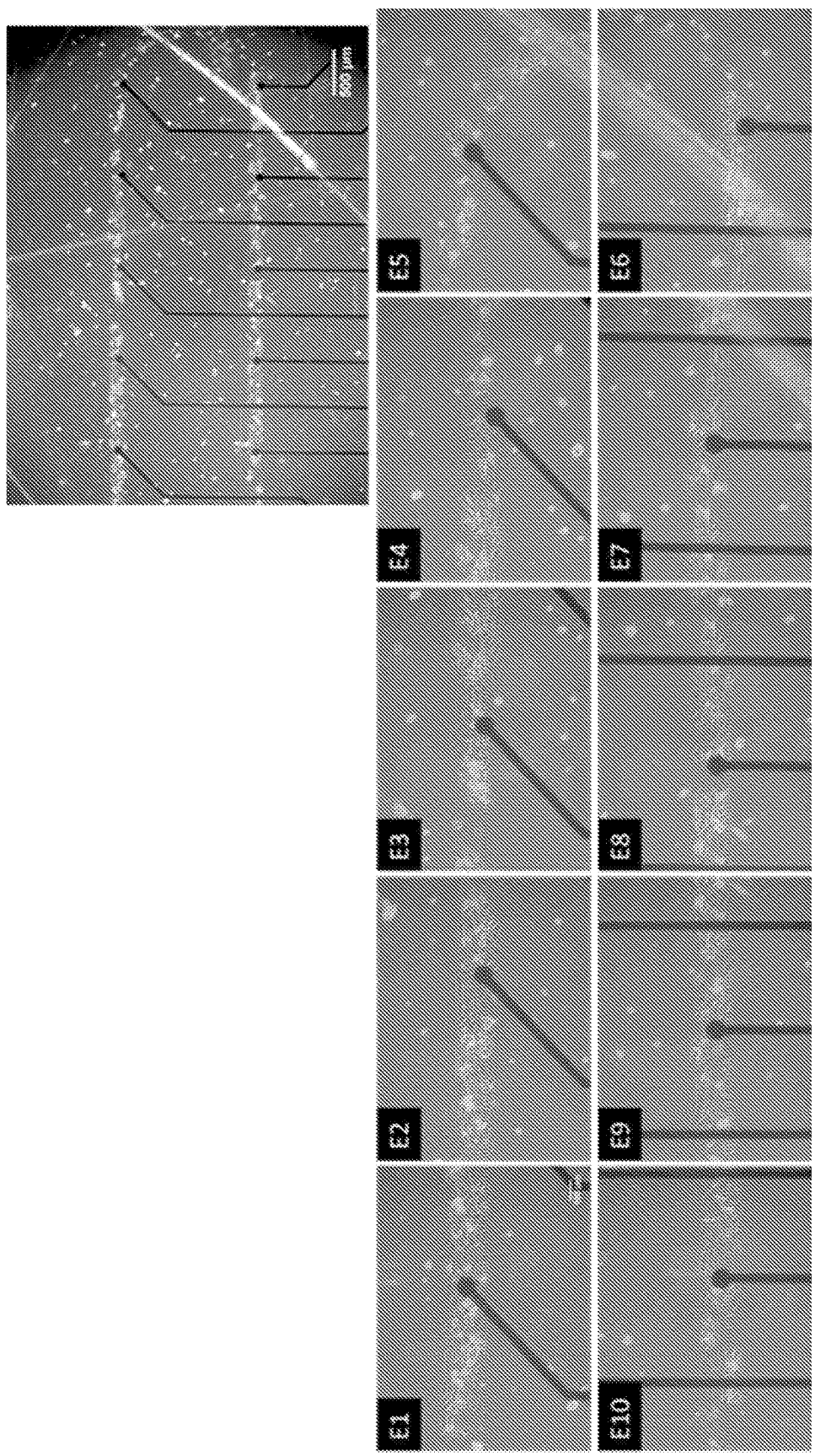
FIG. 8 shows an image of an assembled printed cMEA.
Figure 9:
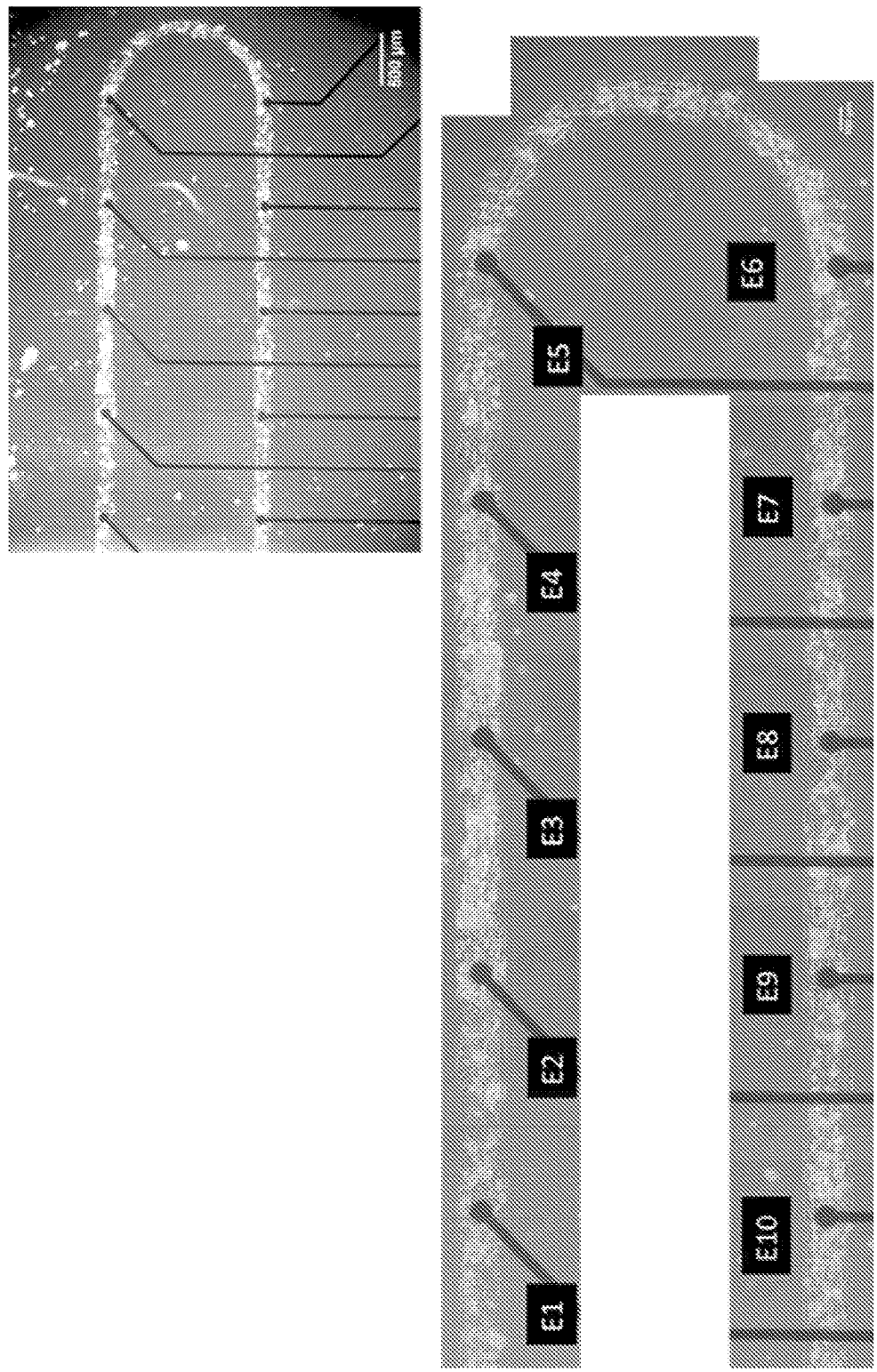
FIG. 9 shows an image of an assembled hand plated cMEA.
Figure 10:
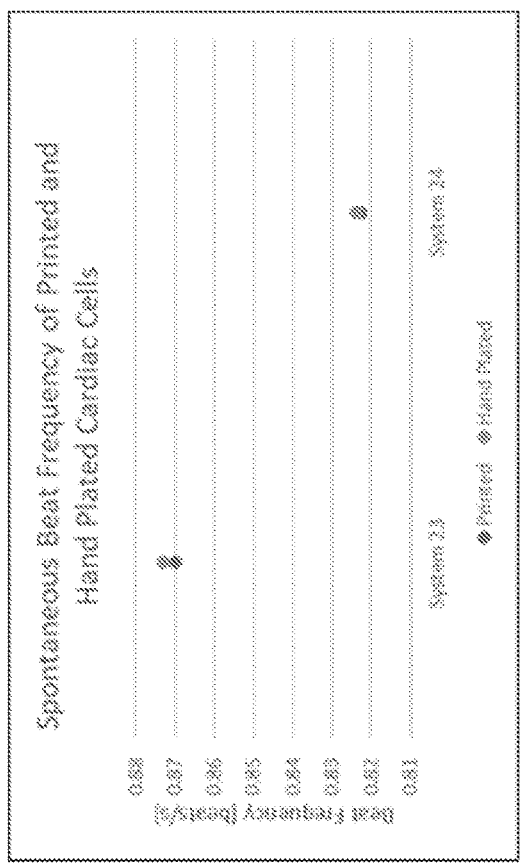
FIG. 10 shows plots comparing spontaneous conduction velocity and beat frequency for printed and hand plated cardiac cells. The standard deviation of the averaged conduction velocity values provided the error bars for the plot of conduction velocities. There was not enough variation in the beat frequency data for visible error bars.
Figure 10:
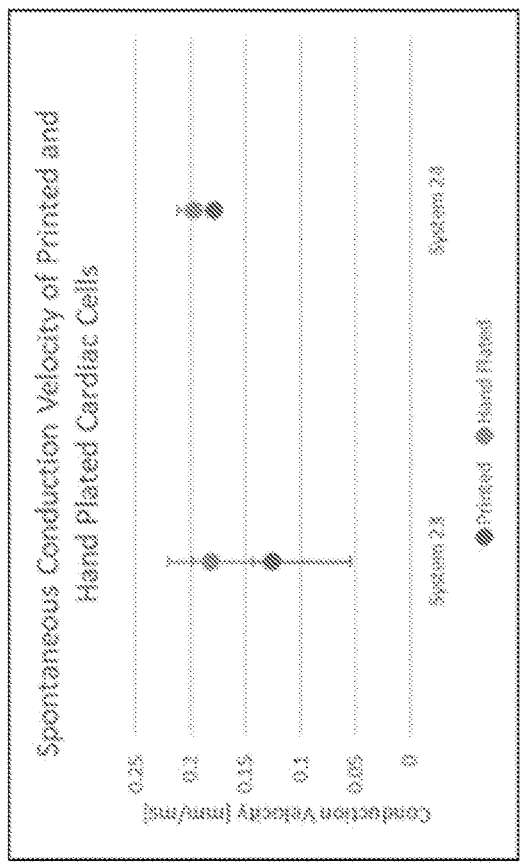

In a different set of experiments human cardiomyocytes were printed. FIG. 7 compares the morphology of the cardiac cells the day after plating, showing that printing cardiac cells does not harm them morphologically. FIG. 8 and FIG. 9 show the assembled printed and hand plated cMEAs, respectively. Both cMEAs exhibit beating cells in a U pattern. Since more cells were used in the hand plating control, there are no breaks in the U pattern as noted in FIG. 9. Even though the U pattern was not complete in FIG. 8, there were still a few connected electrodes to show proof of principle for using the printer to print cardiac cells and allowed for the spontaneous electrical cellular activity measurements shown in FIG. 10, indicating functional cardiac maturation of printed cells. Beat frequency and conduction velocity of printed cells was very similar to hand plated cells. Furthermore calculations were performed showing the significant cost savings for the ideal printing conditions of one vial of cells, assuming $1,000 per vial and 4 million cardiac cells per vial, with results shown in Table 1.

TABLE 1

Savings comparison between printing and hand plating cardiac cells

| Metric | Printing | Hand Plating |
|---|---|---|
| Cells used per cMEA surface | 6,000 | 50,000 |
| Surfaces plated per vial | 666 | 80 |
| Cost per chip | $1.50 | $12.50 |
| Cost to plate 100 surfaces | $150 | $1250 |

Figure 11:
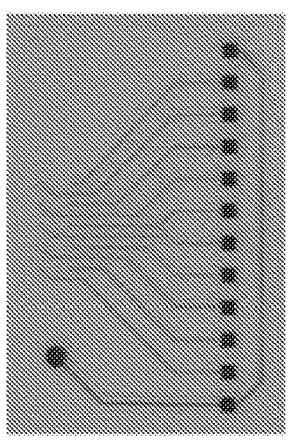
FIG. 11 shows a DETA only coated surface (schematic shown in blue above). (L) Image one day after printing human motoneurons, showing the desired pattern of dots of cells on the electrodes and a line of cells across the bottom electrodes (R) same surface, 16 days after printing.
Figure 11:
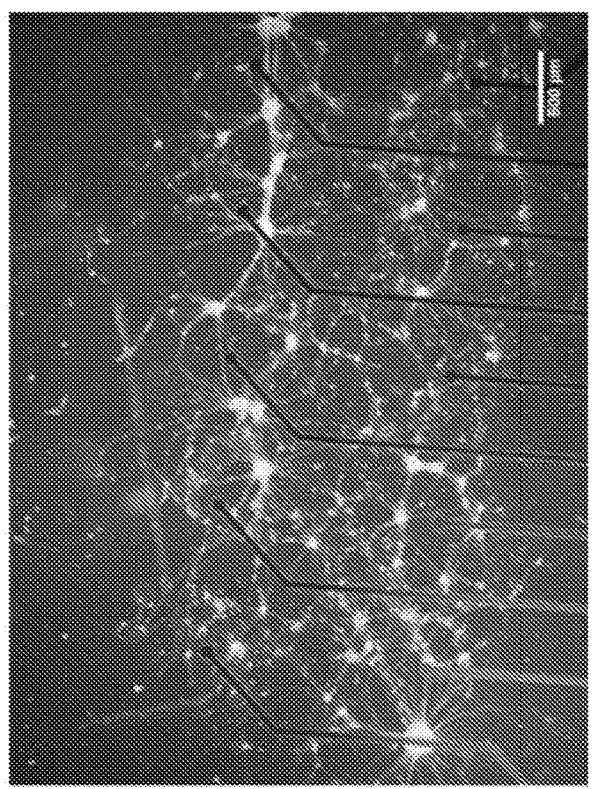
Figure 11:
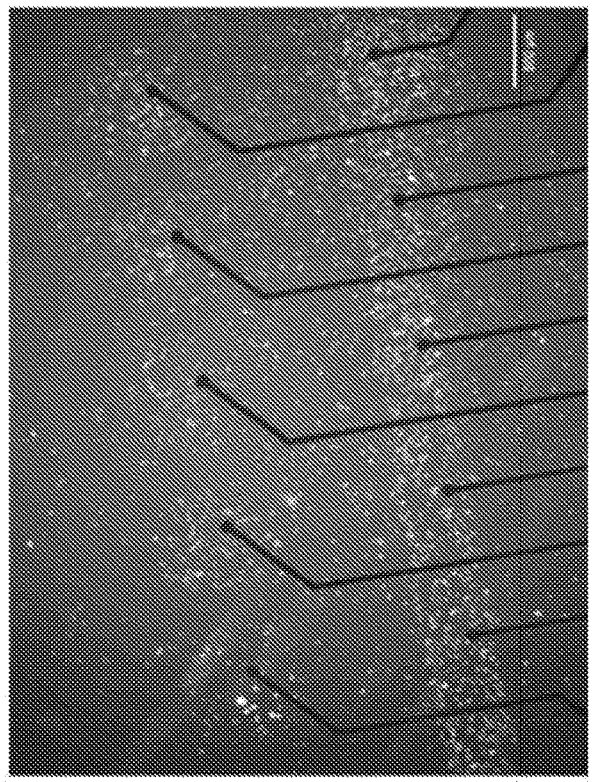
Figure 12:
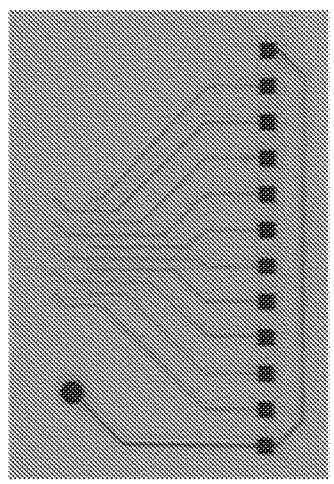
FIG. 12 shows the importance of surface patterning for printing of human motoneurons (hMNs), with corresponding surface patterns shown above each figure. DETA is cytophylic, while PEG is cytophobic. (L) shows DETA/PEG patterned surface 37 days after printing, with the hMNs remaining on the electrodes. (R) shows DETA only coated surface 16 days after printing.
Figure 12:
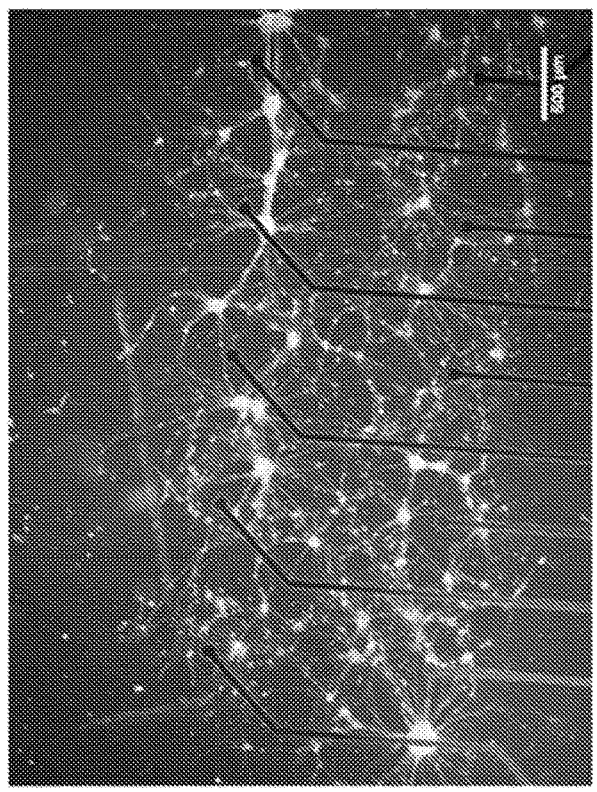
Figure 12:
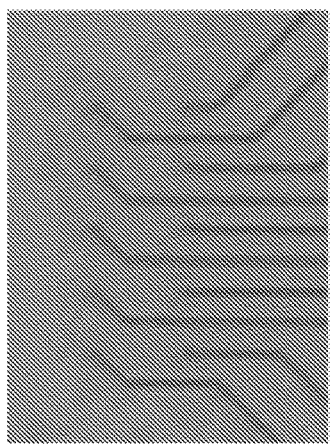
Figure 12:
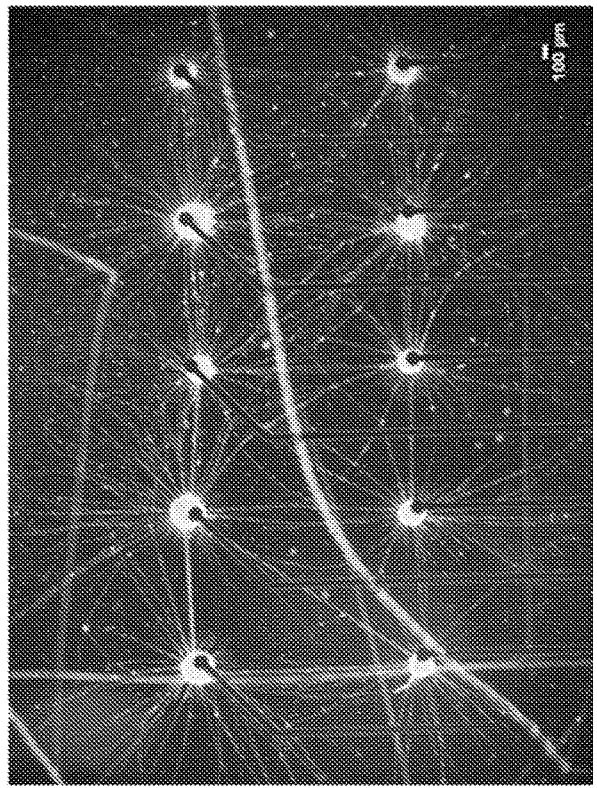
Figure 13:
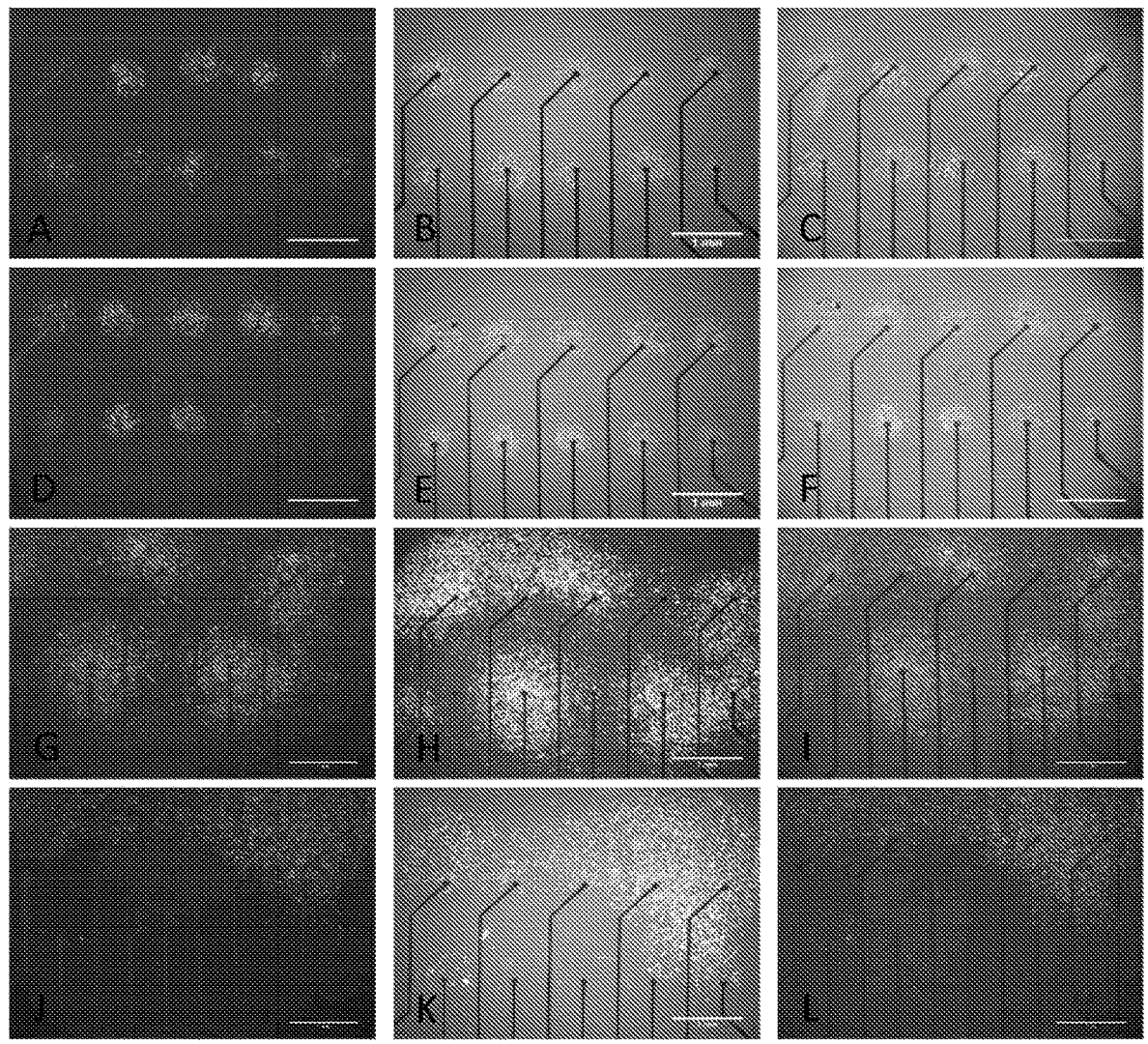
FIG. 13 shows images for hand plating and printing cMEAs. All scale bars are 1 mm. The top row of electrodes were printed using a valve opening time of 400 µs, while the second row was printed using a valve opening time of 250 µs. The third and fourth rows show hand plating attempts. A, D, G, J. Fluorescent image. B, E, H, K. Phase image. C, F, I, L. Combined phase and fluorescent image.

FIG. 11 and FIG. 12 illustrate the benefits of printing on patterned surfaces. Though the cells on the DETA only surface were printed on the electrodes, as seen in FIG. 11, the cells did not remain on the electrodes, and are no longer patterned as desired on day 16. FIG. 12 shows the ability to control the location of the printed human motoneurons on the surface of the electrodes past 28 days using PEG coated, DETA backfilled patterned cMEAs.

Figure 14:
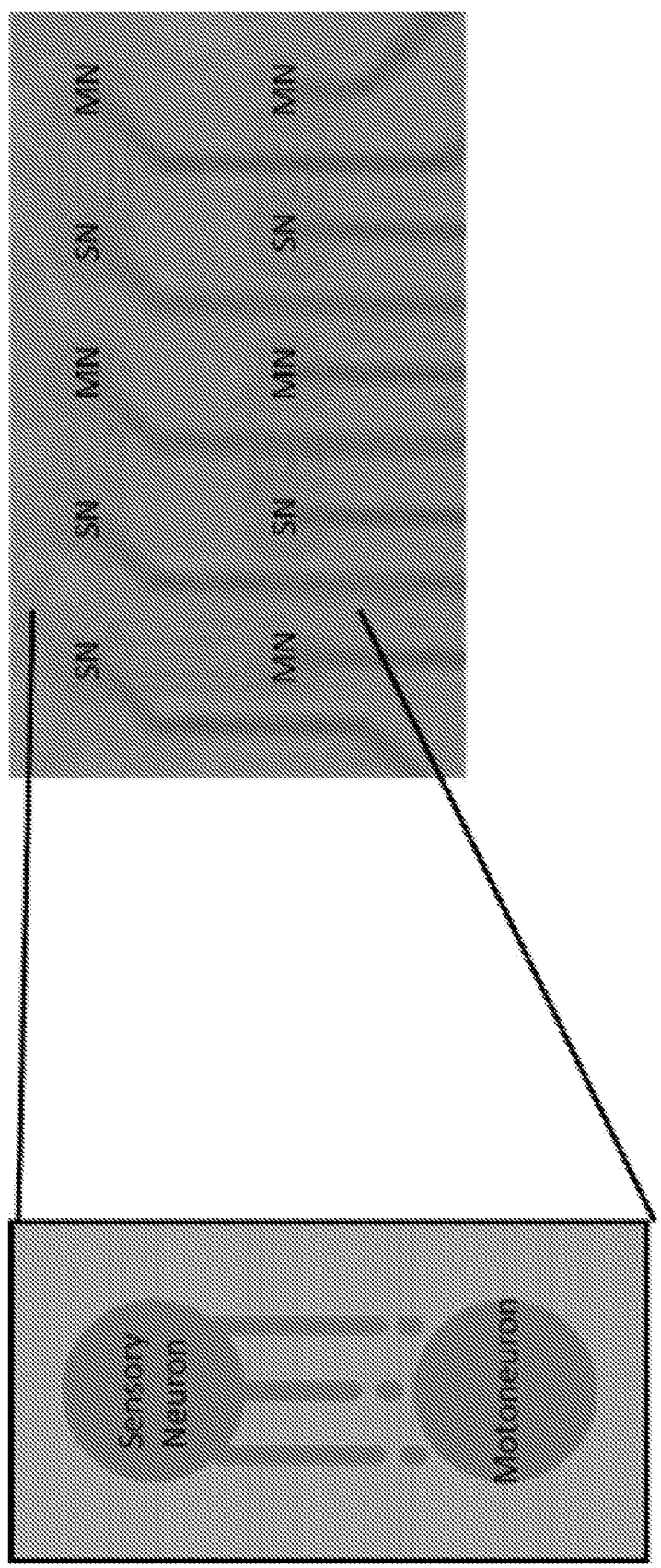
FIG. 14 is a schematic showing a simplified, enlarged view of the pattern (left) and the complete pattern of the cMEA chip (right).
Figure 15:
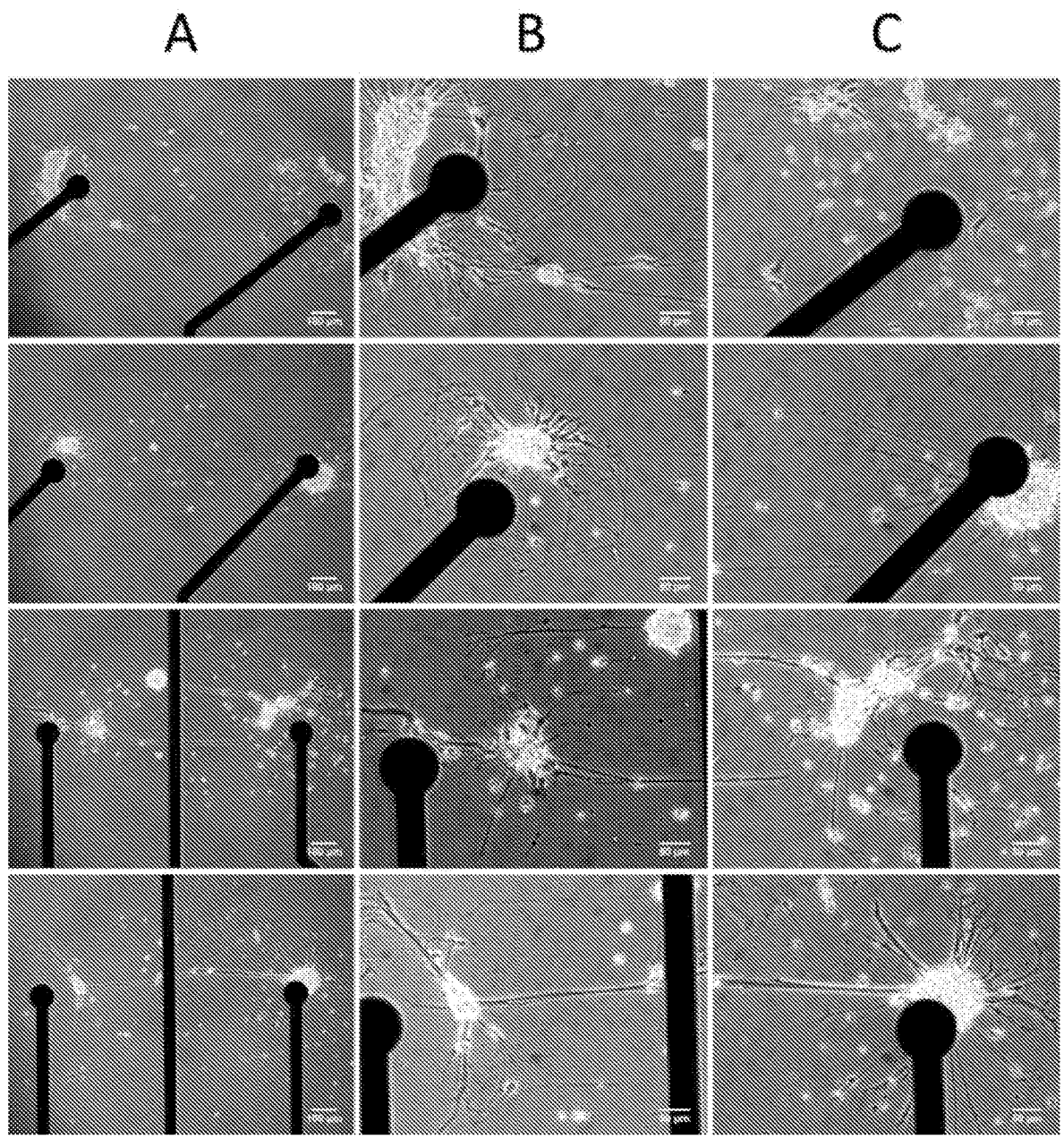
FIG. 15 shows the printing and characterization of several cell types onto one surface to create multicellular networks. Images of innervated printed human motoneurons (hMNs) and human sensory neurons (hSNs) twelve days after printing. Column A shows the two cells connected on the electrodes at 25×. The left electrode contains hMN cells, while the right electrode contains hSN cells. Column B shows a close up of the hMN electrode. Column C shows a close-up of the hSN electrode. Columns B and C images are at 250×.
Figure 16:
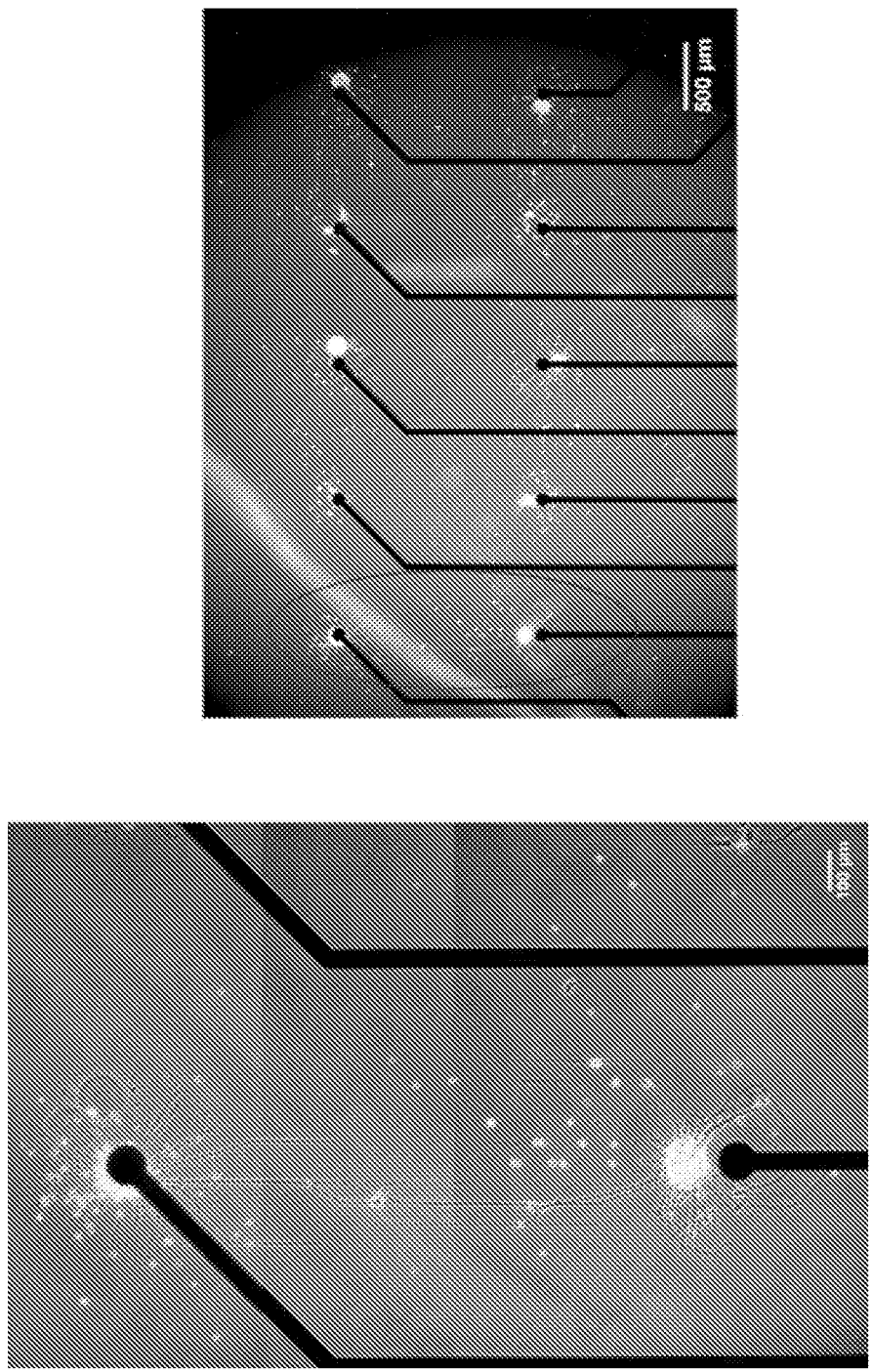
FIG. 16 shows: at left, an image of innervated printed hMNs and hSNs twelve days after printing at 100×. The top electrode contains hSN cells, while the bottom electrode contains hMN cells. At Right, the location of left image on its cMEA chip at 25×.
Figure 17:
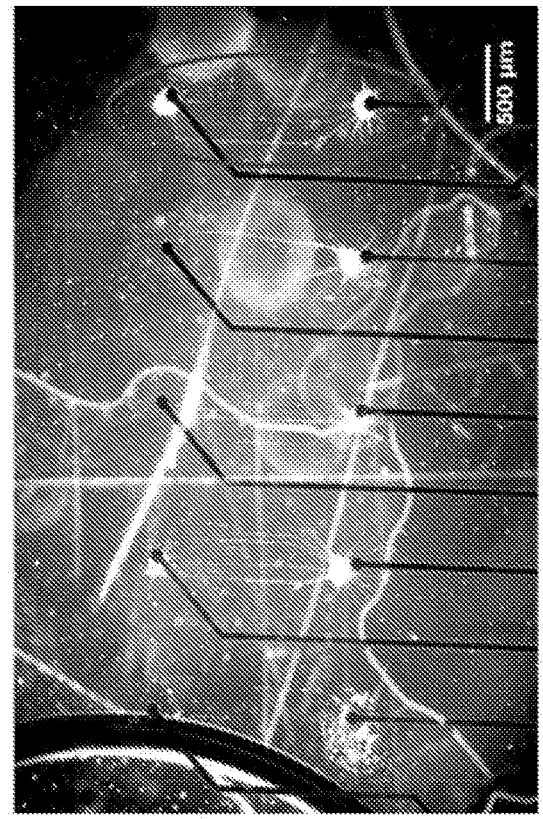
FIG. 17 shows an image of innervated printed hMNs and hSNs fifteen days after printing at 100×. The top electrode contains hSN cells, while the bottom electrode contains hMN cells. R: Location of left image on its cMEA chip at 25×.
Figure 17:
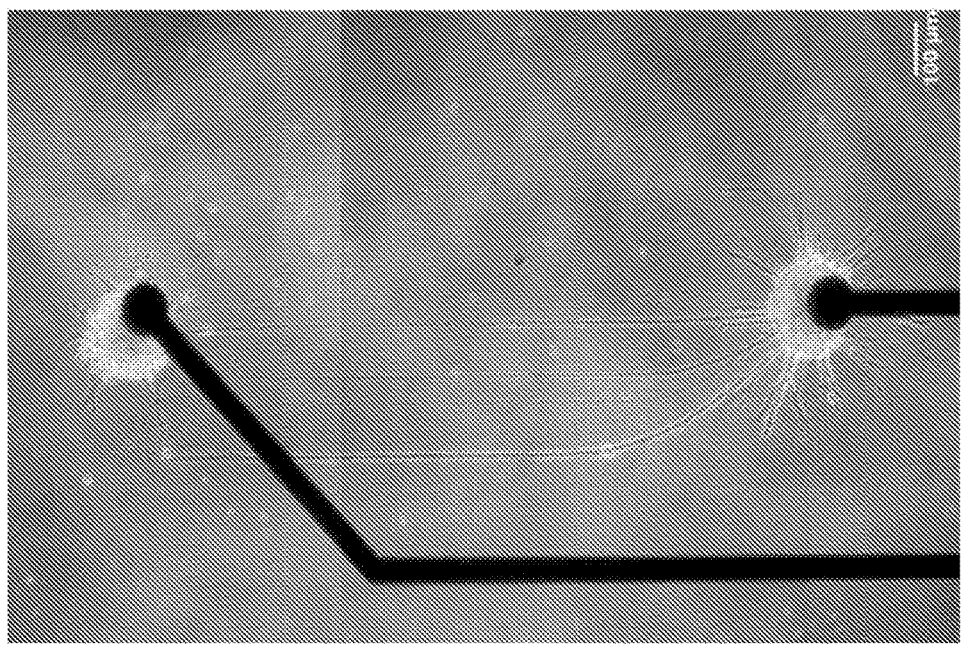

The bioprinting technique further offers the flexibility to print a number of different cell types individually on specific surfaces (FIG. 2, FIG. 3) or to print a combination of several cell types to create more complex cellular networks (FIG. 15, FIG. 16, and FIG. 17). As an example, spinal cord derived human motoneurons were printed onto the cytophilic area on single electrodes of custom-fabricated multi-electrode arrays and maintained in serum free cell culture media over a time period of 28 days (FIG. 3). FIG. 14 shows the pattern for printing a combination of cell types to create more complex cellular networks, in this example human sensory neurons and human motoneurons. The human sensory neurons were printed on the top or left electrodes, and the lines are to encourage the growth of sensory neuron axons towards the location where the human motoneurons were printed. The breaks in the lines near the human motoneuron electrodes were designed to discourage the growth of motoneuron axons toward sensory neurons. FIGS. 15-17 show the results of the print of those two cell types in more detail.

Overall, the method generates precisely defined cell cultures with high cell survivability and functionality for at least 28 days after the printing process. The cell printing approach therefore represents an excellent procedure to streamline current cell culture techniques and is expected to pave the way for larger scale experiments to improve the production of bioMEMS devices and to advance the research on body-on-a-chip devices.

Example 2—Method for Bioprinting Human Motor Neurons

The following method is an example of a method for printing human motoneurons (hMNs). Cells were printed using a regenHU™ 3D Discovery Fluid Dispenser (Villaz-St-Pierre, Switzerland) adapted with a custom acrylic enclosure and a latex skirt to obtain a semi-sterile environment. The instrument was further equipped with a humidifier to optimize humidity inside the printing chamber. The cell suspension was dispensed at low air pressure from the dispenser cartridges using a contactless dispensing mode (jetting) through a microvalve with the dispensed volume being adjusted via the microvalve opening time. The print patterns were created using BioCAD (regenHU™)

Customized acrylic printer plates were used to hold and align the substrates to the printer printing channel. In this example, the substrates were microelectrode arrays that had been pre-patterned with cell adhesive regions. The printer plate 2 is shown in FIG. 18, holding cMEAs 4. The printer plate 2 was scaled to the dimension of standard cell culture plates to fit into the stage of the regenHU™ bioprinter. The printer plate 2 was designed in Autodesk® Inventor® Pro and translated into a laser cutter (Universal® Laser Systems Versalaser® PLS 75 W laser cutter) to machine the custom parts. The parts were then merged using a small volume of dichloromethane to obtain a watertight seal and leak tested before use. Metal pins 6 were pressed into laser etched holes to enable the alignment of the cMEAs 4. The printer plates were cleaned in a 1% tergazyme solution, thoroughly rinsed with MilliQ® water and sterilized with absolute ethanol before use. The printer plate design included a raised platform 8 for the cMEA, thus creating a reservoir under the surface that was filled with cell culture medium shortly before the print while keeping the top of the surface dry. The fabrication protocol included creation of a water reservoir 10 between the wells of the customized printer plate, which was filled with sterile water during printing to ensure humidification of the printing chamber and prevent evaporation of the printed droplets.

Human motoneurons (hMNs) were printed from a cell suspension with hMN medium containing OptiPrep™ (5% vol/vol) and an antibiotic and an antimycotic (1% vol/vol) to prevent cells from possible contamination during the printing process. The OptiPrep™ is a density gradient medium often used for cell isolation. It was added to the cell suspension to decrease the effects of cell settling in the cartridge and thus to increase uniformity and reproducibility of the print pattern. The cell densities within the cell suspension was about $5 \times 10^6$ to $6 \times 10^6$ cells/mL. After the cells were printed, the printer plates were placed into an incubator for 30 minutes to allow for sufficient adherence of the cells onto the cMEA before adding more medium. The cMEAs were transferred into regular cell culture plates the day after the print and medium was changed partially every 4 days.

Example 3—Volumes, Density, and Efficiency Considerations

Figure 19:
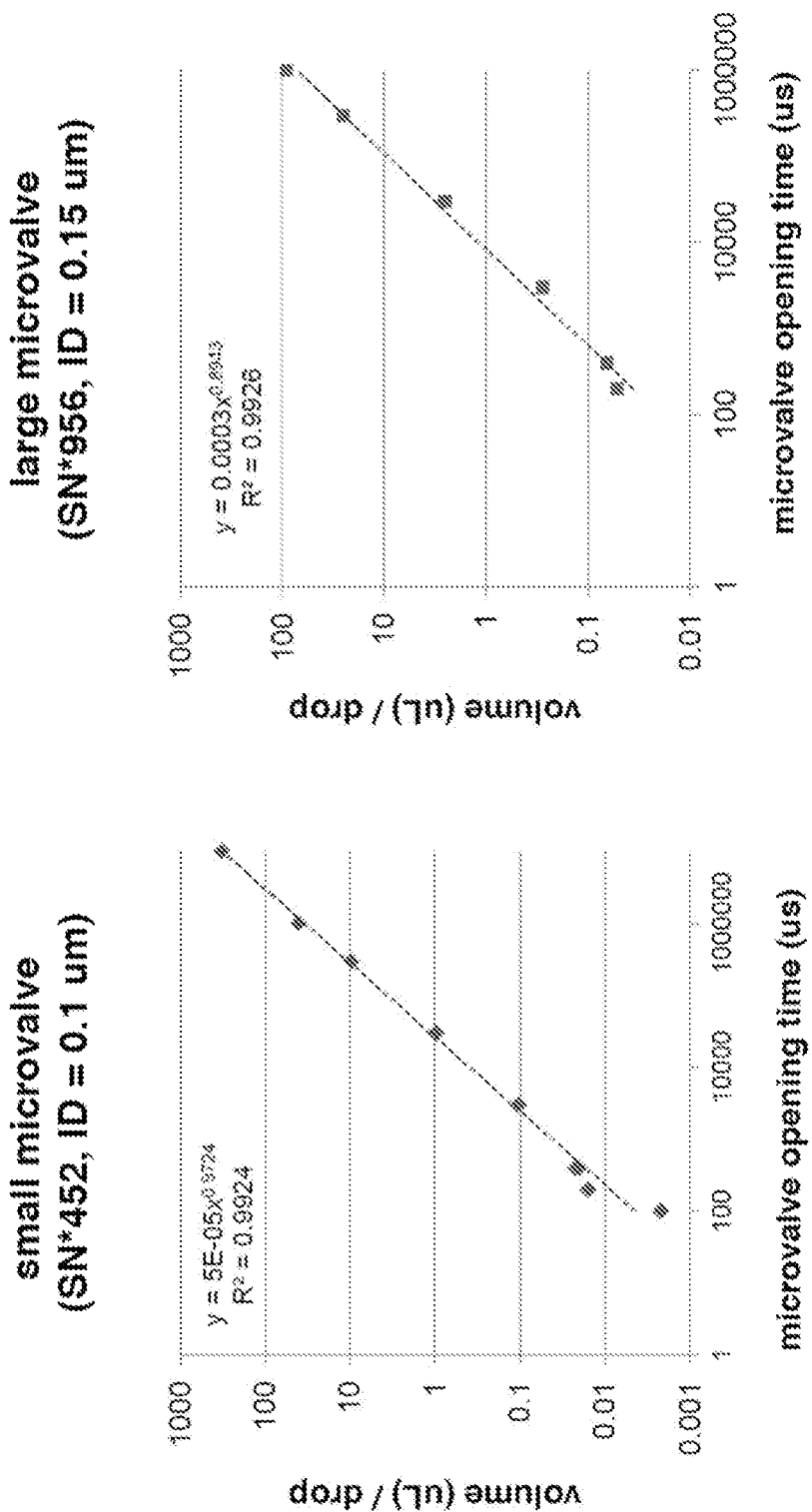
FIG. 19 shows graphs of the effect of microvalve opening time on cell suspension droplet size.
Figure 20:
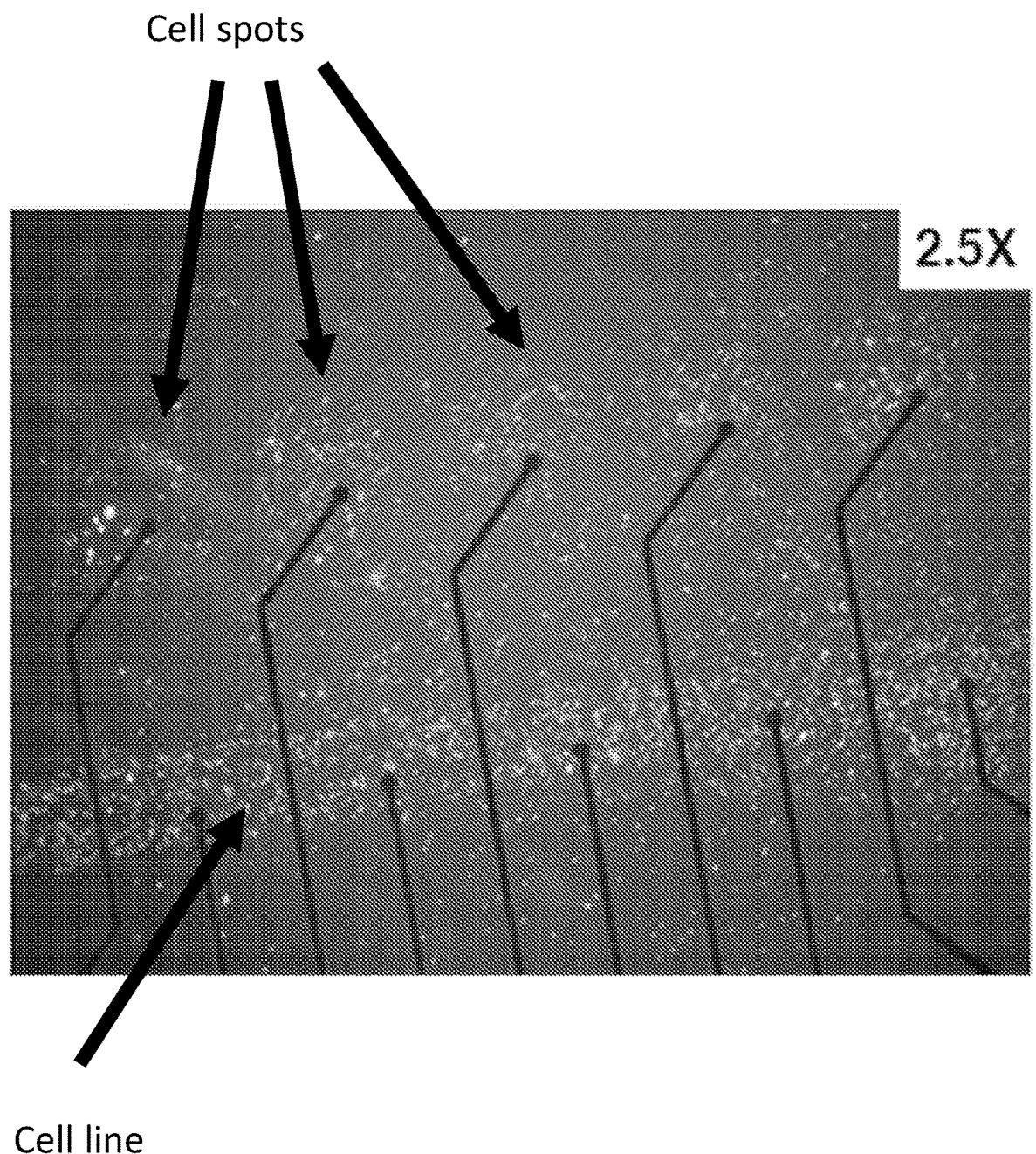
FIG. 20 shows how the bioprinting method can be used to create cell spots or a cell line.

The size of the droplet of cell suspension can be varied by altering the duration of the opening of the microvalve, or the choice of larger or small microvalve, as shown in FIG. 19. Print settings for forming a cell spot (see FIG. 20) might include opening a microvalve for 400 microseconds. Print settings for forming a line might include opening a microvalve for 100 microseconds. The dosing distance can be 0.07-0.08 millimeters with a feed rate of 20 millimeters per second. A dispensed volume of cell suspension for a cell spot can be 0.02 microliters. A dispensed volume of cell suspension for a cell line can be 0.95 microliters.

The following calculations are exemplary for a substrate having a U-shaped cell adhesion pattern, similar to that shown in FIG. 8. For dense patterning, a suggested cell density on the substrate is about 1,000 cells/mm². The U-shaped pattern can, for example, have a surface area of 6 mm². Thus, the number of cells required to cover the U-shaped pattern are 1,000 cells/mm²×6 mm²=6,000 cells. To compare this with hand plating, the entire area of the two dimensional surface might be 50 mm² To obtain dense patterning over the U-shaped area, a density of 1,000 cells/mm² must be delivered over the entire 50 mm² surface. Thus, 50,000 cells are used in the hand plating method. The non-adherent cells are washed off. An efficiency equation to compare the printing method to the hand plating method is shown below. Assuming 80-100% survivability and recovery, the cell printing method uses 12-14% of the cells required by the hand plating method.

$$\frac{6{,}000 \text{ cells printed}}{50{,}000 \text{ cells hand plated}} * S_T * S_P = 1 \quad \text{Equation 1}$$

$S_T$ = survivability/recovery due to trypsinization $S_P$ = survivability/recovery of the printed cells The following calculations are exemplary for patterning over cantilever sensors, such as those shown in FIG. 2. For dense patterning, a suggested cell density on the substrate is about 1,000 cells/mm². The cantilevers can have, for example, a surface area of 3.5 mm². However, because the resolution of the cell printer can vary, the print area may be up to 20 mm². Thus, the number of cells required to cover the cantilevers can be as little as 1,000 cells/mm²×3.5 mm²=3,500 cells or as many as 1,000 cells/mm2×20 mm²=20,000 cells, depending upon the resolution of the cell printer. With hand plating, a large droplet containing 500,000 cells is typically applied to the cantilever surface, and the non-adherent cells are washed off. An efficiency equation to compare the printing method to the hand plating method is shown below. Assuming 100% survivability and recovery, the cell printing method uses 0.7-4% of the cells required by the hand plating method depending upon the resolution of the cell printer.

$$\frac{3{,}500 \text{ to } 20{,}000 \text{ cells printed}}{500{,}000 \text{ cells hand plated}} * S_T * S_P = 1 \quad \text{Equation 2}$$

$S_T$ = survivability/recovery due to trypsinization $S_P$ = survivability/recovery of the printed cells Example 4—Cell Density and Viability Using a cell suspension concentration of $5 \times 10^6$ to $6 \times 10^6$ cells/mL, and adding the minimum amount of cell suspension that can be added to a printer cartridge (125 microliters), the following data were obtained.

TABLE 2

Cell count before print and from dispensed volume:

| SC hMN (Apr. 12, 2016) | cell density (alive cells) (cells/mL) | alive cells (%) | cells/ surface* |
|---|---|---|---|
| before printer | 12.1 * 10^6 | 81 | |
| before 1st print | 12.0 * 10^6 | 77 | 12,000 |
| after 1st print (5 surfaces) | 28.9 * 10^6 | 80 | 28,900 |

TABLE 2-continued

Cell count before print and from dispensed volume:

| SC hMN (Apr. 12, 2016) | cell density (alive cells) (cells/mL) | alive cells (%) | cells/ surface* |
|---|---|---|---|
| after 2nd print (10 surfaces) | 16.8 * 10^6 | 81 | 16,800 |

*assuming 1 uL/print for one surface (expected: 12,000 cells/surface)

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. While the invention has been described with reference to particular embodiments and implementations, it will understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Such equivalents are intended to be encompassed by the following claims. It is intended that the invention not be limited to the particular implementations disclosed herein, but that the invention will include all implementations falling within the scope of the appended claims.

What is claimed is:

1. A method of culturing cells, the method comprising:
  positioning a substrate with pre-patterned cell adhesive regions and pre-patterned cell repulsive regions onto a holding region of a printer plate, the holding region having at least two sides adjacent to a water reservoir containing water, wherein an upper surface of the holding region is higher than a lowest surface of the water reservoir,
  positioning the printer plate onto a printer stage;
  suspending cells in a printing medium to create a cell suspension,
  loading a printer comprising a printing channel with a volume of the cell suspension,
  moving the printer plate and substrate to a position beneath the printing channel,
  aligning a cell adhesive region of the substrate beneath the printing channel of the printer,
  dispensing a plurality of droplets of cell suspension from the printing channel directly onto the cell adhesive region,
  limiting contact of a dispensed cell suspension with cell repulsive regions,
  adhering cells of the dispensed cell suspension to the cell adhesive region to create a cell pattern,
  maintaining the cell pattern in a physiologically suitable environment, and
  humidifying the environment immediately surrounding the dispensed cell suspension via evaporation of water from the water reservoir.

2. The method of claim 1, wherein providing the substrate further comprises pre-patterning the substrate with one or more chemical layers to form the cell adhesive regions and the cell repulsive regions.

3. The method of claim 1, wherein the cell pattern has a width or a length of less than 1 millimeter.

4. The method of claim 1, wherein suspending the cells in a printing medium comprises creating a cell suspension at a concentration of from 0.5 million to 20 million cells per milliliter.

5. The method of claim 1, further comprising preventing cell settling within the print medium.

6. The method of claim 5, wherein preventing cell settling comprises mixing the print medium with an agent that prevents cell settling.

7. The method of claim 1, wherein the print medium has a viscosity of less than 5 centipoise at 37 degrees Celsius.

8. The method of claim 1, wherein a volume of a single printed droplet is less than 2 microliters.

9. The method of claim 8, wherein the volume of a single printed droplet is less than 0.1 microliters.

10. The method of claim 1, wherein the cell adhesive regions have a total cell adhesive surface area, and dispensing a plurality of droplets comprises dispensing from 0.05 microliters to 2 microliters of cell suspension per millimeter squared of the total cell adhesive surface area.

11. The method of claim 1, wherein the cell adhesive regions have a total cell adhesive surface area, and wherein a total number of dispensed cells is from 500 cells per millimeter squared of the total cell adhesive surface area to 2000 cells per millimeter squared of the total cell adhesive surface area.

12. The method of claim 1, wherein the plurality of droplets is dispensed onto a contact region comprising a contact region surface area, and wherein greater than 80% of the contact region surface area is a part of a cell adhesive region.

13. The method of claim 1, wherein limiting contact with cell repulsive regions comprises continuously validating the position of the plurality of droplets as they are being dispensed.

14. The method of claim 1, wherein humidifying the environment further comprises preventing evaporation of the dispensed cell suspension by continuously maintaining a humidified environment around the dispensed cell suspension.

15. The method of claim 14, further comprising fabricating the printer plate that comprises the water reservoir.

16. The method of claim 1, wherein the cell adhesive regions are positioned over sensors, and wherein maintaining the cell pattern comprises keeping a majority of the cells on the substrate confined to positions over the sensors for periods of greater than 5 days.

17. The method of claim 1, wherein dispensing a plurality of droplets of cell suspension creates a first layer of cells, and wherein the method further comprises dispensing additional layers of cells on top of the first layer of cells to create a three dimensional cell structure.

18. The method of claim 1, wherein the printing medium comprises a cell culture media.

19. The method of claim 1, wherein suspending cells in a printing medium comprises suspending more than one cell type in the printing medium, thereby creating a cell pattern with multiple cell types.

20. The method of claim 1, wherein positioning the substrate onto the holding region comprises positioning the substrate above a reservoir of the printer plate, the reservoir at least partially surrounding the holding region.

21. The method of claim 1, wherein positioning the substrate further comprises placing the substrate within a holding chamber defined by walls of the holding region.

22. The method of claim 1, further comprising securing the substrate to the holding region.

23. The method of claim 1, wherein aligning a cell adhesive region of the substrate beneath the printing channel of the printer comprises moving the printer plate to a predetermined position beneath the printing channel.

* * * * *